United States Patent

Bonse et al.

Patent Number: 5,821,222
Date of Patent: *Oct. 13, 1998

[54] CYCLIC DEPSIPEPTIDES HAVING 18 RING ATOMS FOR COMBATING ENDOPARASITES

[75] Inventors: Gerhard Bonse, Köln; Michael Londershausen, Erkrath; Erwin Bischoff, Wuppertal; Hartwig Müller, Velbert; Achim Harder, Köln; Nobert Mencke, Leverkusen; Peter Kurka, Hilden; Peter Jeschke, Leverkusen; Jürgen Scherkenbeck, Wermelskirchen, all of Germany

[73] Assignee: Bayer Aktiengesellschaft, Leverkusen, Germany

[*] Notice: The term of this patent shall not extend beyond the expiration date of Pat. Nos. 5,628,897 and 5,589,503.

[21] Appl. No.: 728,106

[22] Filed: Oct. 9, 1996

Related U.S. Application Data

[63] Continuation of Ser. No. 343,517, filed as PCT/EP93/01436 Jun. 7, 1993 published as WO93/25543, abandoned.

[30] Foreign Application Priority Data

Jun. 11, 1992 [DE] Germany .......................... 42 19 157.2
May 26, 1993 [DE] Germany .......................... 43 17 458.2

[51] Int. Cl.$^6$ .............................. A61K 38/15; C07K 11/02
[52] U.S. Cl. .................................. 514/11; 514/9; 514/2; 530/317; 530/343
[58] Field of Search ..................... 514/11, 9, 2; 530/317, 530/343

[56] References Cited

U.S. PATENT DOCUMENTS

| | | | |
|---|---|---|---|
| 5,116,815 | 5/1992 | Takagi et al. | 514/11 |
| 5,589,503 | 12/1996 | Mencke et al. | 514/450 |
| 5,624,897 | 4/1997 | Jeschke et al. | 514/11 |

FOREIGN PATENT DOCUMENTS 0382173  8/1990  European Pat. Off. .

OTHER PUBLICATIONS

Helvetica Chimica Acta, vol. 46, 1963, No. 98, pp. 927–935; "Synthesen in der Depsipeptid–Reihe", Pl.A. Plattner et al.
Helvetica Chimica Act, vol. 46, 1963, No. 185, pp. 1715–1720; "Synthesen in der Depsipeptid–Reihe", P. Quitt et al.

Chem. Ber., vol. 101, 1968, pp. 1532–1539; "Synthese von Stereoisomeren des Enniatins B", G. Losse et al.

Agric. Biol. Chem., vol. 43, No. 5, 1979, pp. 1079–1083; "Synthese of Bassianolide and Its Two Homologs, . . . ", M. Kanaoka et al.

Tetrahedron Letters, vol. 2, pp. 159–162, 1971; "The Synthesis and Some Properties of Beauvericin", Yu.A. Ovchinnikov et al.

The Journal of Antibiotics, vol. 45, No. 8, 1992, pp. 1207–1215; "New Cyclodepsipeptides, Enniatins D, E, and F . . . ", H. Tomoda et al.

Zh. Obshch. Khim, vol. 38, No. 6, 1968, pp. 1228–1239; "Relation Between Structure and Biological Action in a Series of . . . ", I.I. Mikhaleva et al.

Mikhaleva et al, Zh. Obshch. Khim., vol. 38(6), pp. 1228–1239, (1968); Chem. Abs. 69.

Morrison, Organic Chemistry, 3rd ed., pp. 79–81.

*Primary Examiner*—Ponnathapura Achutamurthy
*Assistant Examiner*—T. D. Wessendorf
*Attorney, Agent, or Firm*—Sprung Kramer Schaefer & Briscoe

[57] ABSTRACT

The present invention relates to the use of cyclic depsipeptides having 18 ring atoms of the general formula (I)

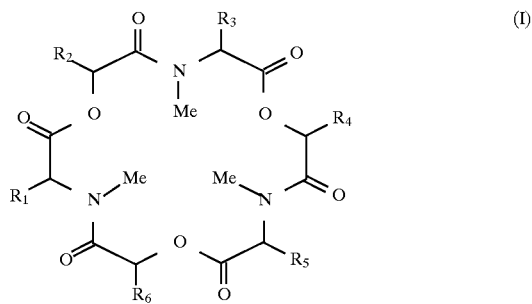

in which $R^1$ to $R^6$ have the meaning given in the description, and to their optical isomers and racemates, in medicine and veterinary medicine for combating endoparasites, to their preparation, and to new cyclic depsipeptides having 18 ring atoms.

3 Claims, No Drawings

CYCLIC DEPSIPEPTIDES HAVING 18 RING ATOMS FOR COMBATING ENDOPARASITES

This application is a continuation of application Ser. No. 08/343,517, filed as PCT/EP93/01436 jun. 7, 1993 published as WO93/25543, now abandoned.

The present invention relates to the use of cyclic depsipeptides having 18 ring atoms for combating endoparasites, to novel cyclic depsipeptides having 18 ring atoms, and to processes for their preparation.

Certain cyclic depsipeptides having 18 ring atoms (enniatins) and processes for their preparation are already known (cf. for example: Hiroshi Tomoda et al. J. Antibiotics 45 (1992) pp. 1207–1215 [enniatins A, A$_1$, B, B$_1$, D, E and F]; P. Quitt et al., Helv. Chimica Acta 46 (1963) pp. 1715–1720; P. Quitt et al., Helv. Chimica Acta 47 (1964) pp. 166–173 [Enniatin A]).

However, nothing has been disclosed as yet about a use of these compounds against endoparisites (cf. Merck Index, 10th Edition, p. 517, No. 3543).

The present invention relates to:

1. The use of cyclic depsipeptides having 18 ring atoms of the general formula (I)

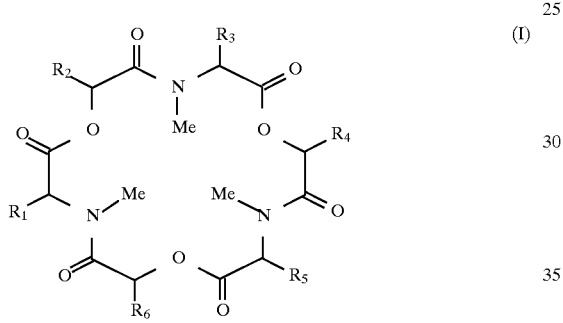

in which
  $R^1$, $R^3$ and $R^5$ independently of one another represent straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, or alkoxycarbonylaminoalkyl, 9-fluorenylmethoxycarbonyl(Fmoc)aminoalkyl, alkenyl, cycloalkyl, cycloalkylalkyl and optionally substituted arylalkyl, substituents which may be mentioned being halogen, hydroxyl, alkyl or alkoxy,
  $R^2$, $R^4$ and $R^6$ independently of one another represent straight-chain or branched alkyl having up to 8 carbon atoms, hydroxyalkyl, alkanoyloxyalkyl, alkoxyal-kyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl optionally substituted aryl or arylalkyl, substituents which may be mentioned being halogen, hydroxyl, alkyl or alkoxy, and their optical isomers and racemates,
in medicine and veterinary medicine for combating endoparasites.

2. New cyclic depsipeptides having 18 ring atoms of the general formula (Ia)

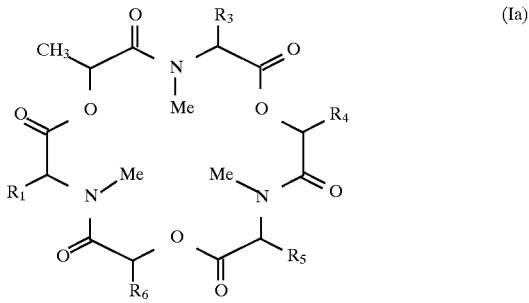

in which $R^1$ represents straight-chain or branched alkyl having 2 to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, or alkoxycarbonylaminoalkyl, 9-fluorenylmethoxycarbonyl(Fmoc)aminoalkyl, alkenyl, cycloalkyl, cycloalkylalkyl and optionally substituted arylalkyl, substituents which may be mentioned being halogen, hydroxyl, alkyl or alkoxy, $R^3$ and $R^5$ independently of one another represent straight-chain or branched alkyl having up to 8 carbon atoms hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, or alkoxycarbonylaminoalkyl, 9-fluorenylmethoxycarbonylaminoalkyl, alkenyl, cycloalkyl, cycloalkylalkyl and optionally substituted arylalkyl, substituents which may be mentioned being halogen, hydroxyl, alkyl or alkoxy, $R^2$, $R^4$ and $R^6$ independently of one another represent straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxacarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl and optionally substituted aryl or arylalkyl, substituents which may be mentioned being halogen, hydroxyl, alkyl or alkoxy, and their optical isomers and racemates.

3. Processes for the preparation of cyclic depsipeptides having 18 ring atoms of the general formula (I)

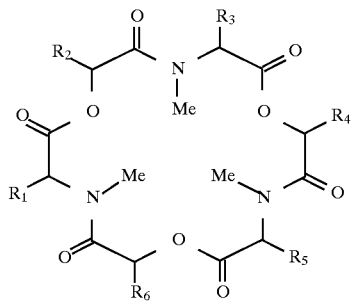

(I)

R[1], R[3] and R[5] independently of one another represent straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, or alkoxycarbonylaminoalkyl, 9-fluorenylmethoxycarbonyl(Fmoc)aminoalkyl, alkenyl, cycloalkyl, cycloalkylalkyl and optionally substituted arylalkyl, substituents which may be mentioned being halogen, hydroxyl, alkyl or alkoxy, R[2], R[4] and R[6] independently of one another represent straight-chain or branched alkyl having up to 8 carbon atoms, hydroxyalkyl, alkanoyloxyalkyl, alkoxyal-kyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl optionally substituted aryl or arylalkyl, substituents which may be mentioned being halogen, hydroxyl, alkyl or alkoxy, characterized in that a) carboxyl-activated open-chain hexadepsipeptides of the general formula (IIc)

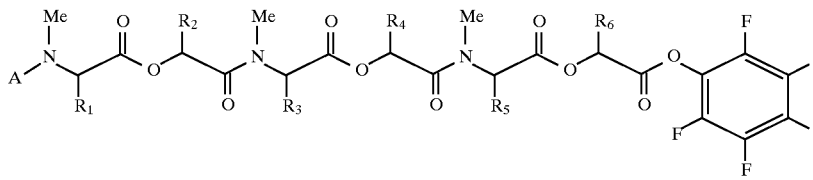

in which

A represents an amino protective group which can be detached selectively with regard to the active ester protecting group, such as benzyl or benzyloxycarbonyl, and R[1], R[2], R[3], R[4], R[5] and R[6] have the abovementioned meaning, are cyclized in the presence of a hydrogenation catalyst, in the presence of a basic reaction auxiliary and in the presence of a diluent, or b) open-chain hexadepsipeptides of the general formula (IId)

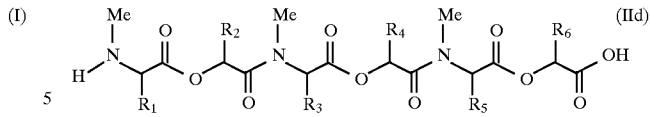

in which

R[1], R[2], R[3], R[4], R[5] and R[6] have the abovementioned meaning, are cyclized in the presence of a coupling reagent, in the presence of a basic reaction auxiliary and in the presence of a diluent.

4. Open-chain hexadepsipeptides of the general formula (II)

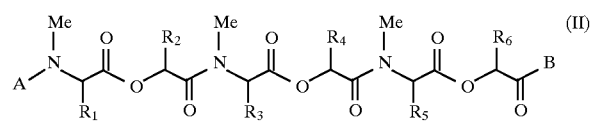

in which

A represents hydrogen or benzyl or a group of the formula —CO—R[7]

in which

R[7] represents straight-chain or branched alkoxy, alkenoxy or arylalkoxy having up to 6 carbon atoms in the alkyl moiety, for example tert-butoxycarbonyl (Boc), benzyloxycarbonyl (Z), ethoxycarbonyl (EtOC), allyloxycarbonyl (AllOC), fluorenyl-9-methoxycarbonyl (Fmoc) or methoxycarbonyl (MetOC), R[1], R[2], R[3], R[4], R[5] and R[6] have the meaning given under item 2, B represents hydroxyl, halogen or an active ester protecting group which acts to protect and simultaneously activate the carboxyl group, such as pentafluorophenoxy.

5. Processes for the preparation of the open-chain hexadepsipeptides of the general formula (II)

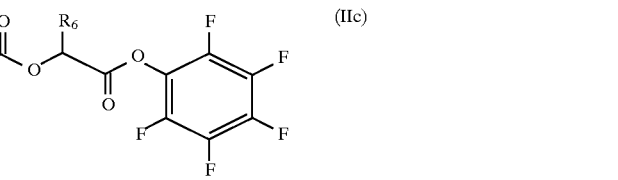

in which

A and B have the meaning given under item 4,

R[1], R[2], R[3], R[4], R[5] and R[6] have the abovementioned meaning, characterized in that a) tetradepsipeptides of the general formula (IIIb)

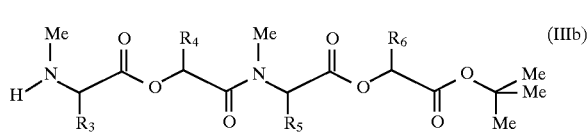

in which

R$^3$, R$^4$, R$^5$ and R$^6$ have the abovementioned meaning, are reacted, in a first reaction step, with didepsipeptides of the general formula (IVb)

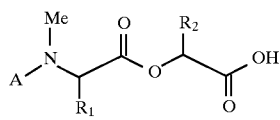

in which

A has the meaning given under item 4,

R$^1$ and R$^2$ have the abovementioned meaning, in the presence of a coupling reagent, in the presence of a basic reaction auxiliary and in the presence of a diluent, then, in a second reaction step, the resulting hexadepsipeptide of the general formula (IIa)

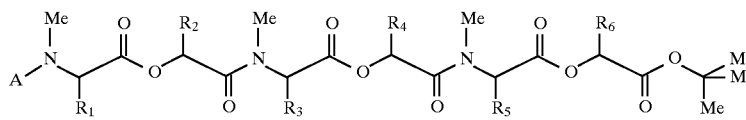

in which

A has the meaning given under item 4,

R$^1$, R$^2$, R$^3$, R$^4$, R$^5$ and R$^6$ have the abovementioned meaning, is subjected to C-terminal hydrolysis in the presence of a diluent and in the presence of a protonic acid, and then the carboxyl group is halogenated for activation or converted into an active ester protecting group, for example the pentafluorophenyl ester group, or in that b) the open-chain hexadepsipeptides which can be obtained, for example, in accordance with process 5a, of the general formula (IIa)

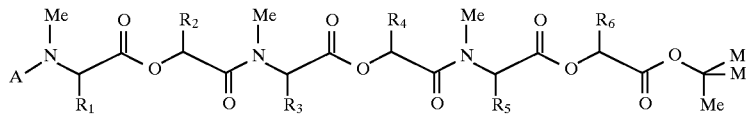

in which

A has the meaning given under item 4,

R$^1$, R$^2$, R$^3$, R$^4$, R$^5$ and R$^6$ have the abovementioned meaning, are subjected to C-terminal hydrolysis in a first reaction step in the presence of a diluent and, if appropriate, in the presence of a protonic acid, then, in a second reaction step, the resulting open-chain hexadepsipeptide of the general formula (IIb)

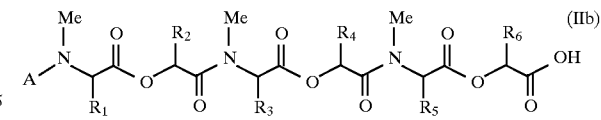

in which

A has the meaning given under item 4,

R$^1$, R$^2$, R$^3$, R$^4$, R$^5$ and R$^6$ have the abovementioned meaning, is subjected to N-terminal deblocking in the presence of a diluent and in the presence of a catalyst.

6. Tetradepsipeptides of the general formula (III)

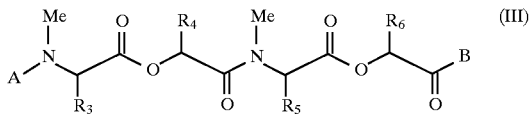

in which

A and B have the meaning given under item 4,

R$^3$, R$^4$, R$^5$ and R$^6$ have the meaning given under item 2,

7. Process for the preparation of the tetradepsipeptides of the general formula (III)

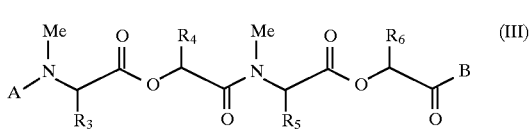

in which

A and B have the meaning given under item 4,

R$^3$, R$^4$, R$^5$ and R$^6$ have the meaning given under item 2, characterized in that in the event that B represents tert-butoxy, didepsipeptides of the general formula (Vb)

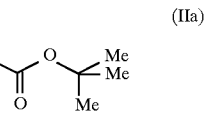

in which

A, R$^3$ and R$^4$ have the abovementioned meaning, are reacted, in a first reaction step, with didepsipeptides of the general formula (VIb)

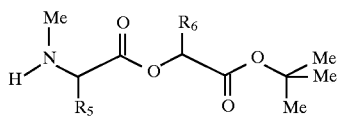 (VIb)

in which $R^5$ and $R^6$ have the abovementioned meaning, in the presence of a coupling reagent, in the presence of a basic reaction auxiliary and in the presence of a diluent, then, in a second reaction step, the resulting tetradepsipeptide of the general formula (IIIa)

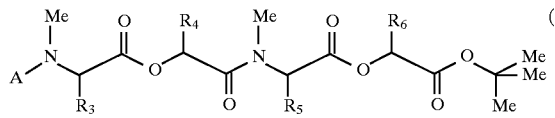 (IIIa)

in which

A, $R^3$, $R^4$, $R^5$ and $R^6$ have the abovementioned meaning, is subjected to N-terminal deblocking in the presence of a diluent and in the presence of a suitable catalyst.

8. Didepsipeptides of the general formula (IV)

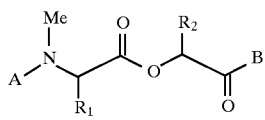 (IV)

in which

A and B have the meaning given under item 4 and $R^1$ and $R^2$ have the meaning given under item 2.

9. Process for the preparation of the didepsipeptides of the general formula (IV)

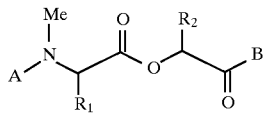 (IV)

in which

A and B have the meaning given under item 4, $R^1$ and $R^2$ have the meaning given under item 2, characterized in that in the event that B represents hydroxyl, N-methyl-amino acids of the general formula (VII)

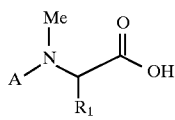 (VII)

in which

A and $R^1$ have the abovementioned meaning, in a first reaction step, with alkali metal salts of the formula (VIII)

$M^+X^-$ (VIII)

in which

M represents a monovalent alkali metal cation, preferably lithium, sodium, potassium or caesium, in particular caesium, and X represents a halide or carbonate anion, preferably carbonate anion, then, in a second reaction step, the resulting alkali metal salt of the formula (VIIa)

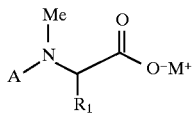 (VIIa)

in which

A and $R^1$ have the abovementioned meaning,

M represents a matal cation equivalent which is bonded in a salt-like manner, is reacted with 2-halogeno-carboxylic acid derivatives as alkylating agent of the general formula (IX)

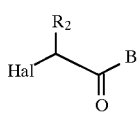 (IX)

in which $R^2$ and B have the abovementioned meaning and

Hal represents halogen, preferably chlorine, bromine or iodine, in particular bromine or chlorine, in the presence of a diluent, and then, in a third reaction step, in the event that B represents tert-butoxy, the resulting didepsipeptide of the general formula (IVa)

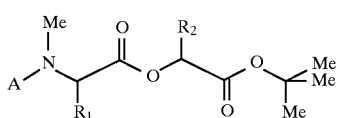 (IVa)

in which

A, $R^1$ and $R^2$ have the abovementioned meaning, is subjected to C-terminal hydrolysis in the presence of a diluent and, if appropriate, in the presence of a protonic acid.

10. Didepsipeptides of the general formula (V)

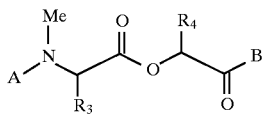 (V)

in which

A and B have the meaning given under item 4, $R^3$ and $R^4$ have the meaning given under item 2, 11. Process for the preparation of the didepsipeptides of the general formula (V)

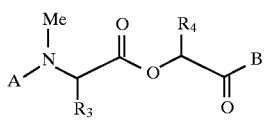 (V)

in which

A and B have the meaning given under item 4, $R^3$ and $R^4$ have the meaning given under item 2, characterized in that in the event that B represents hydroxyl, N-methyl-amino acids of the general formula (X)

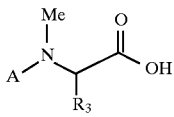

in which

A and $R^3$ have the abovementioned meaning, in a first reaction step, with alkali metal salts of the formula (VIII)

 (VIII)

in which

M and X have the meaning given under item 9, then, in a second reaction step, the resulting alkali metal salt of the formula (Xa)

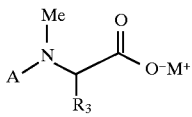 (Xa)

in which

A, $R^3$ and M have the meaning given under item 9, is reacted with 2-halogeno-carboxylic acid derivatives as alkylating agent of the general formula (XI)

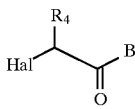 (XI)

in which

B, $R^2$ and Hal have the meaning given under item 9, in the presence of a diluent, then, in a third reaction step, in the event that B represents tert-butoxy, the resulting didepsipeptide of the general formula (Va)

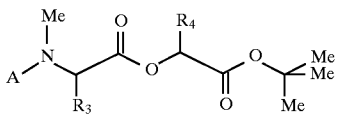 (Va)

A, $R^3$ and $R^4$ have the abovementioned meaning, is subjected to C-terminal hydrolysis in the presence of a diluent and, if appropriate, in the presence of a protonic acid.

12. Didepsipeptides of the general formula (VI)

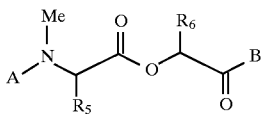 (VI)

in which

A and B have the meaning given under item 4, $R^5$ and $R^6$ have the meaning given under item 2, 13. Process for the preparation of the didepsipeptides of the general formula (VI)

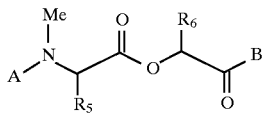 (VI)

in which

A and B have the meaning given under item 4, $R^5$ and $R^6$ have the meaning given under item 2, and their stereoisomers which are possible, characterized in that in the event that B represents hydrogen, N-methyl-amino acids of the general formula (XII)

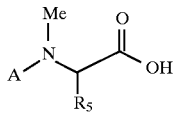 (XII)

in which

A and $R^5$ have the abovementioned meaning, in a first reaction step, with alkali metal salts of the formula (VIII)

 (VII)

in which

M and X have the meaning given under item 9, then, in a second reaction step, the resulting alkali metal salt of the formula (XIIa),

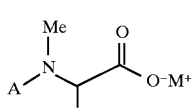 (XIIa)

in which

A, $R^5$ and M have the meaning given under item 9, is reacted with 2-halogeno-carboxylic acid derivatives as suitable alkylating agent of the general formula (XIII)

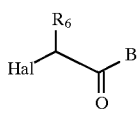 (XIII)

in which

B, $R^6$ and Hal have the abovementioned meaning, in the presence of a diluent, and then, in a third reaction step, in the event that B represents tert-butoxy, the resulting didepsipeptide of the general formula (VIa)

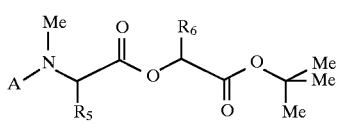 (VIa)

in which

A, $R^5$ and $R^6$ have the abovementioned meaning, is subjected to N-terminal deblocking in the presence of a of a catalyst and in the presence of a diluent.

The compounds of the general formula (I) are outstandingly suitable for combating endoparasites, in particular in the field of veterinary medicine.

Formula (I) provides a general definition of the cyclic depsipeptides having 18 ring atoms (enniatins) according to the invention.

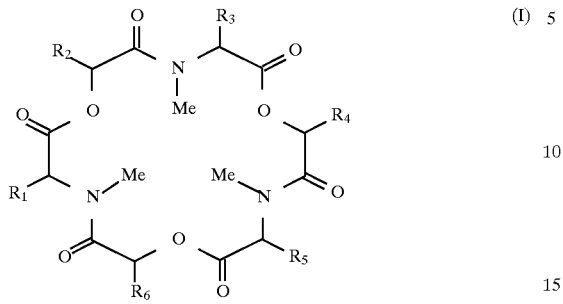

Preferred compounds of the formula (I) are those in which $R^1$, $R^3$ and $R^5$ independently of one another for straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino $C_1$–$C_6$-alkyl, in particular dimethylaminopropyl, dimethylaminobutyl, guanido-$C_1$–$C_6$-alkyl, in particular guanidopropyl, $C_1$–$C_4$-alkoxycarbonylamino-$C_1$–$C_6$-alkyl, in particular tert-butoxycarbonylaminopropyl, tert-butoxycarbonylaminobutyl, 9-fluorenylmethoxycarbonyl(Fmoc)amino-$C_1$–$C_6$-alkyl, in particular 9-fluorenyl-methoxycarbonyl (Fmoc)aminopropyl, 9-fluorenylmethoxycarbonyl (Fmoc)aminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl-$C_1$–$C_4$-alkyl, in particular phenylmethyl which can optionally be substituted by radicals from the series comprising halogen, in particular fluorine, chlorine bromine or iodine, hydroxyl, $C_1$–$C_4$-alkoxy, in particular methoxy or ethoxy, and $C_1$–$C_4$-alkyl, in particular methyl, $R^2$, $R^4$ and $R^6$ independently of one another for straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl-$C_1$–$C_4$-alkyl, in particular phenylmethyl which can optionally be substituted by radicals from the series comprising halogen, in particular fluorine, chlorine bromine or iodine, hydroxyl, $C_1$–$C_4$-alkoxy, in particular methoxy or ethoxy, or $C_1$–$C_4$-alkyl, in particular methyl, and their optical isomers and racemates Particularly preferred compounds of the formula (I) are those in which $R^1$, $R^3$ and $R^5$ independently of one another for straight-chain or branched $C_1$–$C_8$-alkyl, in particular methyl, ethyl, propyl, isopropyl, butyl, isobutyl, sec-butyl, pentyl, isopentyl, sec-pentyl, hexyl, iso-hexyl, hexyl, sec-hexyl, heptyl, isoheptyl, sec-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonylaminopropyl, tert-butoxycarbonylaminobutyl, $C_2$–$C_8$-alkenyl, in particular vinyl, allyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl-$C_1$–$C_4$-alkyl, in particular phenylmethyl which can optionally be substituted by one or more identical or different substituents from amongst those mentioned above, $R^2$, $R^4$ and $R^6$ independently of one another for straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, aryl-$C_1$–$C_4$-alkyloxy-$C_1$–$C_6$-alkyl, in particular benzyloxymethyl, 1-benzyloxyethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl, phenyl-$C_1$–$C_4$-alkyl, in particular phenylmethyl which can optionally be substituted by one or more identical or different radicals from amongst those mentioned above, and their optical isomers and racemates.

Very particularly preferred compounds of the formula (I) are those in which $R^1$, $R^3$ and $R^5$ independently of one another for straight-chain or branched $C_1$–$C_8$-alkyl, in particular methyl, ethyl, propyl, isopropyl, butyl, isobutyl, sec-butyl, pentyl, isopentyl, sec-pentyl, hexyl, iso-hexyl, sec-hexyl, heptyl, isoheptyl, sec-heptyl, octyl, isooctyl, sec-octyl $C_2$–$C_8$-alkenyl, in particular allyl, $C_3$–$C_7$-cycloalkyl-$C_1$–$C_4$-alkyl, in particular cyclohexylmethyl, phenyl-$C_1$–$C_4$-alkyl, in particular phenylmethyl, $R^2$, $R^4$ and $R^6$ independently of one another for straight-chain or branched $C_1$–$C_8$-alkyl, in particular methyl, ethyl, propyl, isopropyl, butyl, isobutyl, sec-butyl, pentyl, isopentyl, sec-pentyl, hexyl, iso-hexyl, sec-hexyl, heptyl, isoheptyl, sec-heptyl, octyl, isooctyl, sec-octyl, $C_2$–$C_8$-alkenyl, in particular vinyl, allyl, $C_3$–$C_7$-cycloalkyl-$C_1$–$C_4$-alkyl, in particular cyclohexylmethyl, phenyl-$C_1$–$C_4$-alkyl, in particular phenylmethyl which can optionally be substituted by one or more identical or different radicals from amongst those mentioned above, and their optical isomers and racemates.

All compounds of the general formula (I) which can exist in optically active, stereoisomeric forms or in the form of racemic mixtures, can be used in the sense of the present invention. However, the optically active, stereo-isomeric forms of the compounds of the general formula (I) are preferably used according to the invention.

The following compounds of the general formula (I) in which the radicals $R^1$ to $R^6$ have the following meaning:

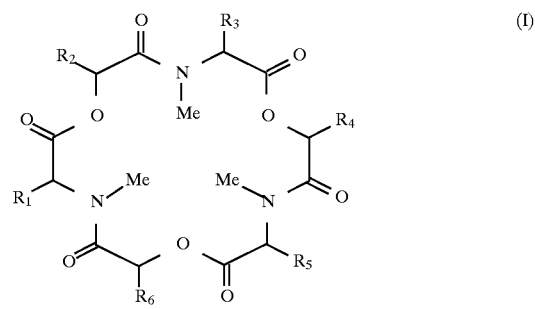

are mentioned individually.

| $R^1$ | $R^2$ | $R^3$ | $R^4$ | $R^5$ | $R^6$ |
| --- | --- | --- | --- | --- | --- |
| —CHMeCH$_2$Me | -cyclohexyl | —CHMeCH$_2$Me | —Me | —CHMeCH$_2$Me | —Me |
| —CHMeCH$_2$Me | -cyclohexyl | —CHMeCH$_2$Me | —Me | —CHMeCH$_2$Me | -cyclohexyl |
| —CHMeCH$_2$Me | —CH$_2$-Phe | —CHMeCH$_2$Me | —Me | —CHMeCH$_2$Me | —Me |
| —CHMeCH$_2$Me | —CH$_2$-Phe | —CHMeCH$_2$Me | —Me | —CHMeCH$_2$Me | —CH$_2$-Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$-Phe | —CHMeCH$_2$Me | —Me | —CHMeCH$_2$Me | —Me |
| —CH$_2$-Phe | —CHMe$_2$ | —CH$_2$-Phe | —CHMe$_2$ | —CHMeCH$_2$Me | —CHMe$_2$ |
| —CH$_2$CHMe$_2$ | —CH$_2$-Phe | —CH$_2$CHMe$_2$ | —Me | —CH$_2$CHMe$_2$ | —CH$_2$-Phe |
| —(CH$_2$)$_3$—Me | —Me | —CHMeCH$_2$Me | —Me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_2$—Me | —Me | —(CH$_2$)$_2$—Me | —Me | —(CH$_2$)$_2$—Me | —Me |
| —(CH$_2$)$_3$—Me | —Me | —(CH$_2$)$_3$—Me | —Me | —(CH$_2$)$_3$—Me | —Me |
| —CH$_2$—CH=CH$_2$ | —Me | —CH$_2$—CH=CH$_2$ | —Me | —(CH$_2$)—CH=CH$_2$ | —Me |
| —CHMeCH$_2$Me | —Me | —CHMeCH$_2$Me | —Me | —CHMeCH$_2$Me | —CH$_2$—Me |
| —CHMeCH$_2$Me | —Me | —CHMeCH$_2$Me | —Me | —CHMeCH$_2$Me | —(CH$_2$)$_2$—Me |
| —CHMeCH$_2$Me | —Me | —CHMeCH$_2$Me | —Me | —CHMeCH$_2$Me | —(CH$_2$)$_3$—Me |
| —CHMeCH$_2$Me | —Me | —CHMeCH$_2$Me | —Me | —CH$_2$Me | —Me |
| —CHMeCH$_2$Me | —Me | —CHMeCH$_2$Me | —Me | —(CH$_2$)$_2$—Me | —Me |
| -cyclohexyl | —Me | -cyclohexyl | —Me | -cyclohexyl | —Me |
| —CH$_2$CHMe$_2$ | -cyclohexyl | —CH$_2$CHMe$_2$ | —Me | —CH$_2$CHMe$_2$ | -cyclohexyl |
| —CH$_2$CHMe$_2$ | -cyclohexyl | —CH$_2$CHMe$_2$ | —Me | —CH$_2$CHMe$_2$ | —Me |
| —CHMeCH$_2$Me | —CHMe$_2$ | —CHMeCH$_2$Me | —CHMe$_2$ | —CHMeCH$_2$Me | —Me |
| —CH$_2$-Phe | —Me | —CH$_2$-Phe | —Me | —CH$_2$-Phe | —Me |

-continued

| R¹ | R² | R³ | R⁴ | R⁵ | R⁶ |
|---|---|---|---|---|---|
| -cyclohexyl | —Me | -cyclohexyl | —Me | -cyclohexyl | —Me |
| —CHMe₂ | —CHMe₂ | —CHMe₂ | —Me | —CHMe₂ | —Me |
| —CHMe₂ | —CHMe₂ | —CHMe₂ | —CHMe₂ | —CHMe₂ | —Me |
| —CH₂—Me | —CHMe₂ | —CH₂Me | —Me | —CH₂—Me | —Me |
| —CH₂—Me | —CHMe₂ | —CH₂Me | —CHMe₂ | —CH₂—Me | —Me |
| —(CH₂)₂—Me | —CHMe₂ | —(CH₂)₂—Me | —Me | —(CH₂)₂—Me | —Me |
| —(CH₂)₂—Me | —CHMe₂ | —(CH₂)₂—Me | —CHMe₂ | —(CH₂)₂—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |

Me = Methyl; Phe = phenyl;

Preferred and particularly preferred amongst the new compounds of the general formula (Ia) are those in which the substituents have the definitions given above as being preferred.

Some of the compounds of the general formula (I) are known (by isolation, cf., for example: R. Zocher et al., J. Antibiotics 45 (1992) pp. 1273–1277 [enniatins A, B and C]; Hiroshi Tomoda et al. J. Antibiotics 45 (1992) pp. 1207–1215 [enniatins A, A₁, B, B₁, D, E and F]; by synthesis, cf., for example: P. Quitt et al., Helv. Chimica Acta 46 (1963) pp. 1715–1720; P. Quitt et al., Helv. Chimica Acta 47 (1964) pp. 166–173 [enniatin A]; Pl. A. Plattner et al., Helv. Chimica Acta 46 (1963) pp. 927–935 [enniatin B]; Angew. Chem. 102 (1990) pp. 562–563 [fenestin A]; Angew. Chem. 97 (1985) pp. 606–607 [ulicyclamide]; J. Org. Chem. 47 (1982) pp. 3261–3264).

The compounds of the general formula (I) can be prepared by processes a) and b) given above under item 3.

If, in process 3a for the preparation of the new cyclic hexadepsipeptides (enniatins) (I), pentafluorophenyl N-benzyloxycarbonyl-N-methyl-L-isoleucyl-D-lactyl-N-methyl-L-isoleucyl-D-lactyl-N-methyl-L-isoleucyl-D-lactate is employed as compounds of the formula (IIc), the process can be represented by the following equation:

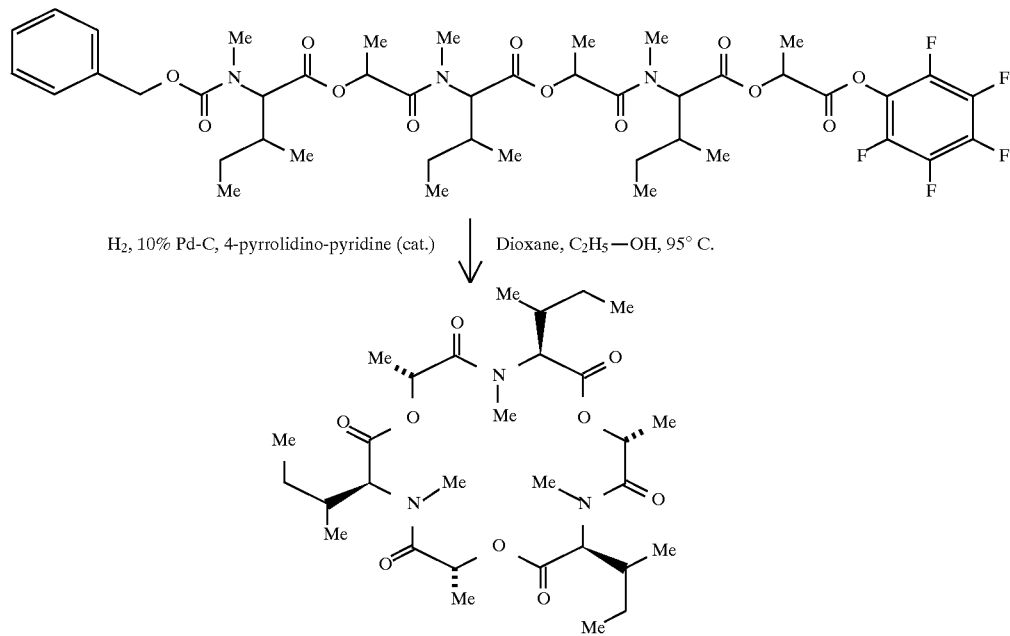

Yu. A. Ovchinnikov et al. Tetrahedron Lett. 2 (1971) pp. 159–162; R. W. Roeske et al. Biochem. Biophys. Res. Commun. 57 (1974) pp. 554–561 [beauvericin]; Yu. A. Ovchinnikov et al. Zh. Obshch. Khim. 42 (10) (1972) pp. 2320–2334; ref. C.A. 78, 58 77 k) or can be obtained by the processes described in these publications.

Surprisingly, it has now been found that the compounds of the formula (I) according to the invention too can be prepared by the process used by U. Schmidt et al., for macrocyclic peptide alkaloids (cf. for example: U. Schmidt et al. in Synthesis (1991) pp. 294–300 [didemnin A, B and C]; Angew. Chem. 96 (1984) pp. 723–724 [dolastatin 3];

Formula (IIc) provides a general definition of the carboxyl-activated derivatives of the open-chain hexadepsipeptides, which are required as starting substances for carrying out process 3a according to the invention. In this formula, A and R¹ to R⁶ preferably represent those radicals which have already been mentioned in connection with the description of the substances of the formula (I) according to the invention as being preferred for these substituents.

The carboxyl-activated pentafluorophenyl esters of the formula (IIc) which are used as starting materials are new. They can be obtained by processes known from the literature (cf. L. Kisfaludy et al. J. Org. Chem. 35 (1970), p. 3563; L.

Kisfaludy et al. J. Org. Chem. 44 (1979), pp. 654–655. Their preparation is described further below.

The following compounds of the general formula (IIc) in which the radicals A and $R^1$ to $R^6$ have the following meaning may be mentioned individually:

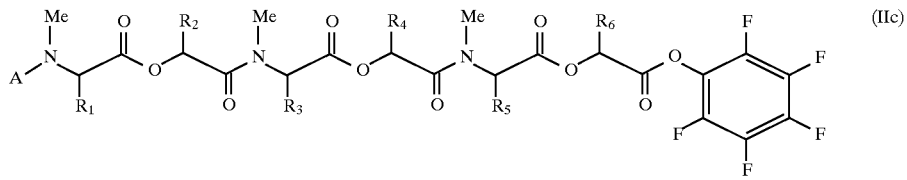

compounds, such as triethylamine, trimethylamine, tribenzylamine, triisopropylamine, tributylamine, tribenzylamine, tricyclohexylamine, triamylamine, trihexylamine, N,N-dimethyl-aniline, N,N-dimethyl-toluidine, N,N-dimethyl-p-aminopyridine, N-methyl-

| A  | $R^1$ | $R^2$ | $R^3$ | $R^4$ | $R^5$ | $R^6$ |
|----|-------|-------|-------|-------|-------|-------|
| Z  | —CHMeCH$_2$Me | -cyclohexyl | —CHMeCH$_2$Me | —Me | —CHMeCH$_2$Me | —Me |
| Bn | —CHMeCH$_2$Me | -cyclohexyl | —CHMeCH$_2$Me | —Me | —CHMeCH$_2$Me | -cyclohexyl |
| Bn | —CHMeCH$_2$Me | —CH$_2$-Phe | —CHMeCH$_2$Me | —Me | —CHMeCH$_2$Me | —Me |
| Bn | —CHMeCH$_2$Me | —CH$_2$-Phe | —CHMeCH$_2$Me | —Me | —CHMeCH$_2$Me | —CH$_2$-Phe |
| Z  | —CHMeCH$_2$Me | —(CH$_2$)$_3$—Me | —CHMeCH$_2$Me | —Me | —CHMeCH$_2$Me | —Me |
| Z  | —CHMeCH$_2$Me | —(CH$_2$)$_3$—Me | —CHMeCH$_2$Me | —Me | —CHMeCH$_2$Me | —Me |
| Bn | —CHMeCH$_2$Me | —(CH$_2$)$_3$—Me | —CHMeCH$_2$Me | —Me | —CHMeCH$_2$Me | —(CH$_2$)$_3$—Me |
| Bn | —CHMe$_2$ | —CH$_2$-Phe | —CHMeCH$_2$Me | —Me | —CHMeCH$_2$Me | —Me |
| Z  | —CH$_2$-Phe | —CHMe$_2$ | —CH$_2$-Phe | —CHMe$_2$ | —CHMeCH$_2$Me | —CHMe$_2$ |
| Bn | —CH$_2$CHMe$_2$ | —CH$_2$-Phe | —CH$_2$CHMe$_2$ | —Me | —CH$_2$CHMe$_2$ | —CH$_2$-Phe |
| Bn | —CH$_2$—Me | —Me | —CH$_2$—Me | —Me | —CH$_2$—Me | —Me |
| Z  | —(CH$_2$)$_2$—Me | —Me | —(CH$_2$)$_2$—Me | —Me | —(CH$_2$)$_2$—Me | —Me |
| Bn | —(CH$_2$)$_3$—Me | —Me | —(CH$_2$)$_3$—Me | —Me | —(CH$_2$)$_3$—Me | —Me |
| Bn | —CH$_2$—CH=CH$_2$ | —Me | —CH$_2$—CH=CH$_2$ | —Me | —CH$_2$—CH=CH$_2$ | —Me |
| Z  | —CHMeCH$_2$Me | —Me | —CHMeCH$_2$Me | —Me | —CHMeCH$_2$Me | —CH$_2$—Me |
| Z  | —CHMeCH$_2$Me | —Me | —CHMeCH$_2$Me | —Me | —CHMeCH$_2$Me | —(CH$_2$)$_2$—Me |
| Z  | —CHMeCH$_2$Me | —Me | —CHMeCH$_2$Me | —Me | —CHMeCH$_2$Me | —(CH$_2$)$_3$—Me |
| Z  | —CHMeCH$_2$Me | —Me | —CHMeCH$_2$Me | —Me | —CH$_2$Me | —Me |
| Z  | —CHMeCH$_2$Me | —Me | —CHMeCH$_2$Me | —Me | —(CH$_2$)$_2$—Me | —Me |
| Bn | -cyclohexyl | —Me | -cyclohexyl | —Me | -cyclohexyl | —Me |
| Z  | —CH$_2$CHMe$_2$ | -cyclohexyl | —CH$_2$CHMe$_2$ | —Me | —CH$_2$CHMe$_2$ | -cyclohexyl |
| Z  | —CH$_2$CHMe$_2$ | -cyclohexyl | —CH$_2$CHMe$_2$ | —Me | —CH$_2$CHMe$_2$ | —Me |
| Z  | —CHMeCH$_2$Me | —CHMe$_2$ | —CHMeCH$_2$Me | —CHMe$_2$ | —CHMeCH$_2$Me | —Me |
| Bn | —CH$_2$-Phe | —Me | —CH$_2$-Phe | —Me | —CH$_2$-Phe | —Me |
| Bn | -cyclohexyl | —Me | -cyclohexyl | —Me | -cyclohexyl | —Me |
| Z  | —CHMe$_2$ | —CHMe$_2$ | —CHMe$_2$ | —Me | —CHMe$_2$ | —Me |
| Z  | —CHMe$_2$ | —CHMe$_2$ | —CHMe$_2$ | —CHMe$_2$ | —CHMe$_2$ | —Me |
| Bn | —CH$_2$—Me | —CHMe$_2$ | —CH$_2$—Me | —Me | —CH$_2$—Me | —Me |
| Bn | —CH$_2$—Me | —CHMe$_2$ | —CH$_2$—Me | —CHMe$_2$ | —CH$_2$—Me | —Me |
| Bn | —(CH$_2$)$_2$—Me | —CHMe$_2$ | —(CH$_2$)$_2$—Me | —Me | —(CH$_2$)$_2$—Me | —Me |
| Bn | —(CH$_2$)$_2$—Me | —CHMe$_2$ | —(CH$_2$)$_2$—Me | —CHMe$_2$ | —(CH$_2$)$_2$—Me | —Me |
| Bn | —(CH$_2$)$_3$—Me | —CHMe$_2$ | —(CH$_2$)$_3$—Me | —Me | —(CH$_2$)$_3$—Me | —Me |
| Bn | —(CH$_2$)$_3$—Me | —CHMe$_2$ | —(CH$_2$)$_3$—Me | —CHMe$_2$ | —(CH$_2$)$_3$—Me | —Me |
| Bn | —CH$_2$—CH=CH$_2$ | —CHMe$_2$ | —CH$_2$—CH=CH$_2$ | —Me | —CH$_2$—CH=CH$_2$ | —Me |
| Bn | —CH$_2$—CH=CH$_2$ | —CHMe$_2$ | —CH$_2$—CH=CH$_2$ | —CHMe$_2$ | —CH$_2$—CH=CH$_2$ | —Me |

Bn: —CH$_2$-phenyl; Z: —CO—O—CH$_2$-phenyl; Me = Methyl; Phe = phenyl.

The compounds of the formula (IIc) are preferably cyclized in the presence of a suitable hydrogenation catalyst and in the presence of a basic reaction auxiliary, using diluents.

Suitable catalysts for carrying out the process 3a according to the invention are all customary hydrogenation catalysts. Catalysts which are preferably used are noble-metal catalysts such as, for example, platinum, platinum oxide, palladium or ruthenium, if appropriate on a suitable support such as, for example, carbon or silicon dioxide.

Basic reaction auxiliaries which can be employed are all suitable acid-binding agents, such as amines, in particular tertiary amines, and also alkali metal compounds and alkaline earth metal compounds.

Examples which may be mentioned are the hydroxides, oxides and carbonates of lithium, sodium, potassium, magnesium, calcium and barium, furthermore other basic pyrrolidine, N-methylpiperidine, N-methyl-imidazole, N-methyl-pyrrole, N-methyl-morpholine, N-methyl-hexamethylenimine, pyridine, 4-pyrrolidino-pyridine, 4-dimethylamino-pyridine, quinoline, α-picoline, β-picoline, isoquinoline, pyrimidine, acridine, N,N,N',N'-tetramethylene-diamine, N,N,N',N'-tetra-ethylenediamine, quinoxaline, N-propyl-diisopropylamine, N-ethyl-diisopropylamine, N,N'-di-methyl-cyclohexylamine, 2,6-lutidine, 2,4-lutidine, triethylenediamine, diazabicyclooctane (DABCO), diazabicyclononene (DBN) or diazabicycloundecene (DBU).

Heteroaromatics such as, for example, pyridine, N-methylimidazole or 4-pyrrolidino-pyridine are preferably used.

Diluents which are suitable for carrying out process 3a according to the invention are all inert organic solvents.

Examples which may be mentioned are: halohydrocarbons, in particular chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, dichlorobenzene, chlorotoluene, trichlorobenzene; alcohols such as methanol, ethanol, isopropanol, butanol; ethers such as ethyl propyl ether, methyl tertbutyl ether, n-butyl ether, di-n-butyl ether, di-isobutyl ether, diisoamyl ether, diisopropyl ether, anisole, phenetole, cyclohexylmethyl ether, diethyl ether, ethylene glycol dimethyl ether, tetrahydrofuran, dioxane, dichlorodiethyl ether; nitrohydrocarbons, such as nitromethane, nitroethane, nitrobenzene, chloronitrobenzene, o-nitrotoluene; nitriles such as acetonitrile, butyronitrile, isobutyronitrile, benzonitrile, m-chlorobenzonitrile; aliphatic, cycloaliphatic or aromatic hydrocarbons, such as heptane, hexane, nonane, cymene, benzine fractions within a boiling point range of 70° C. to 190° C., cyclohexane, methylcyclohexane, petroleum ether, ligroin, octane, benzene, toluene, xylene; esters such as ethyl acetate, isobutyl acetate; amides, for example formamide, N-methylformamide, N,N-dimethylformamide, N-methyl-pyrrolidone; ketones such as acetone, methyl ethyl ketone. Mixtures of the abovementioned solvents and diluents are also suitable.

Ethers, such as, for example dioxane, and mixtures of alcohols and ethers are preferred.

Process 3a is carried out by heating compounds of the formula (IIc) in a diluent under high-dilution conditions in the presence of a basic reaction auxiliary and a suitable hydrogenation catalyst in the presence of hydrogen.

The reaction time is approximately 4 to 20 hours. The reaction is carried out at temperatures between +20° C. and +200° C., preferably between +70° C. and +155° C. The reaction is preferably carried out under an inert gas atmosphere and at the pressure which is established under the reaction conditions when the mixture is heated at the reaction temperature required.

To carry out process 3a according to the invention, a solution of pentafluorophenyl N-benzyloxycarbonyl-N-methyl-L-isoleucyl-D-lactyl-N-methyl-L-isoleucyl-D-lactyl-N-methyl-L-isoleucyl-D-lactate of the formula (IIc) in dioxane is added dropwise in the course of 2 to 10 hours at 95° 1 C. to the rapidly stirred suspension of equimolar amounts of a suitable hydrogenation catalyst, for example palladium/charcoal, in excess dioxane while constantly passing through hydrogen. As catalysts, the solution generally contains 0.5 to 2.5 mol, preferably 1.0 to 2.0 mol, of 4-pyrrolidino-pyridine and 0.5 to 10%, preferably 2 to 5%, of alcohol (based on the solvent).

Besides N-benzyloxycarbonyl-substituted pentafluorophenyl esters of the formula (IIc), it is also possible to use N-benzyl- and N-tert-butoxycarbonyl-substituted pentafluorophenyl esters of the formula (IIc) as an alternative, and the latter compounds can be cyclized in a two-phase system by the method of U. Schmidt (cf. for example: U. Schmidt et al., Synthesis (1991) pp. 294–300 [didemnin A, B and C]).

When the reaction is complete, the reaction mixture is cooled, the entire reaction batch is concentrated in vacuo and extracted using an organic solvent, and the extract is worked up in a manner known per se. The products obtained can be purified in the customary manner by recrystallization, distillation in vacuo or by column chromatography (cf. also Preparation Examples).

Finally, the invention is based on the surprising finding that even C- and N-terminally deblocked open-chain hexapeptides can cyclize in a diluent under high-dilution conditions in the presence of suitable coupling reagents and in the presence of a basic reaction auxiliary.

If, in process 3b for the preparation of the new cyclic hexadepsipeptides (enniatins), N-methyl-L-isoleucyl-D-lactyl-N-methyl-L-isoleucyl-D-lactyl-N-methyl-L-isoleucyl-D-lactic acid is used as compounds of the formula (II), the process can be represented by the following equation:

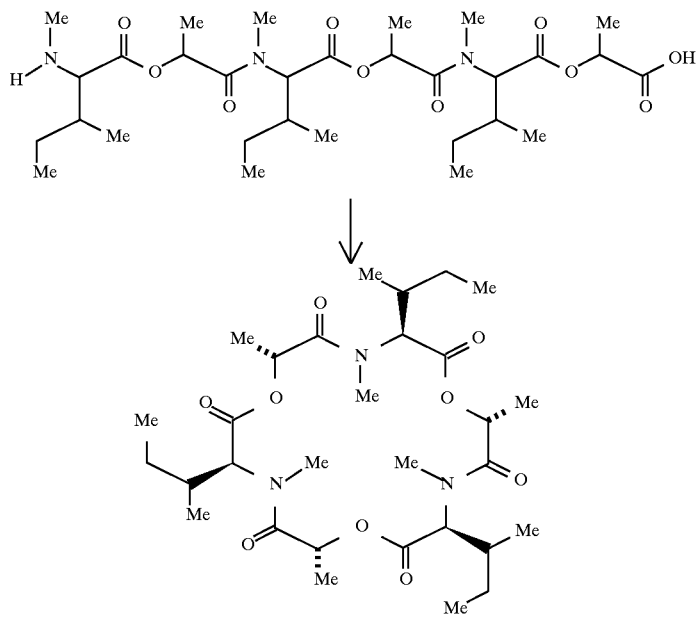

Formula (IId) provides a general definition of the open-chain hexadepsipeptides required as starting substances for carrying out process 3b according to the invention. In this formula, $R^1$ to $R^6$ preferably represent those radicals which have already been mentioned in connection with the description of the substances of the formula (I) according to the invention as being preferred for these substituents.

The hexadepsipeptides of the formula (IId), which are used as starting materials, can be obtained by the processes described further below.

The following compounds of the general formula (IId) in which the radicals $R^1$ to $R^6$ have the following meaning, may be mentioned individually:

with phosphonium reagents, such as benzotriazol-1-yl-oxy-tris(dimethylaminophosphonium) hexafluorophosphate (BOP), bis(2-oxo-3-oxazolidinyl) phosphonium acid chloride (BOP-Cl), or using phosphonic ester reagents, such as diethyl cyanophosphonate (DEPC) and diphenylphosphoryl azide (DPPA), or uronium reagents, such as 2-(1H-

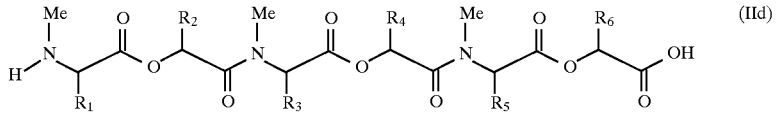

(IId)

| $R^1$ | $R^2$ | $R^3$ | $R^4$ | $R^5$ | $R^6$ |
|---|---|---|---|---|---|
| —CHMeCH$_2$Me | -cyclohexyl | —CHMeCH$_2$Me | —Me | —CHMeCH$_2$Me | —Me |
| —CHMeCH$_2$Me | -cyclohexyl | —CHMeCH$_2$Me | —Me | —CHMeCH$_2$Me | -cyclohexyl |
| —CHMeCH$_2$Me | —CH$_2$-Phe | —CHMeCH$_2$Me | —Me | —CHMeCH$_2$Me | —Me |
| —CHMeCH$_2$Me | —CH$_2$-Phe | —CHMeCH$_2$Me | —Me | —CHMeCH$_2$Me | —CH$_2$-Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$-Phe | —CHMeCH$_2$Me | —Me | —CHMeCH$_2$Me | —Me |
| —CH$_2$-Phe | —CHMe$_2$ | —CH$_2$-Phe | —CHMe$_2$ | —CHMeCH$_2$Me | —CHMe$_2$ |
| —CH$_2$CHMe$_2$ | —CH$_2$-Phe | —CH$_2$CHMe$_2$ | —Me | —CH$_2$CHMe$_2$ | —CH$_2$-Phe |
| —(CH$_2$)$_3$—Me | —Me | —CHMeCH$_2$Me | —Me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_2$—Me | —Me | —(CH$_2$)$_2$—Me | —Me | —(CH$_2$)$_2$—Me | —Me |
| —(CH$_2$)$_3$—Me | —Me | —(CH$_2$)$_3$—Me | —Me | —(CH$_2$)$_3$—Me | —Me |
| —CH$_2$—CH=CH$_2$ | —Me | —CH$_2$—CH=CH$_2$ | —Me | —CH$_2$—CH=CH$_2$ | —Me |
| —CHMeCH$_2$Me | —Me | —CHMeCH$_2$Me | —Me | —CHMeCH$_2$Me | —CH$_2$—Me |
| —CHMeCH$_2$Me | —Me | —CHMeCH$_2$Me | —Me | —CHMeCH$_2$Me | —(CH$_2$)$_2$—Me |
| —CHMeCH$_2$Me | —Me | —CHMeCH$_2$Me | —Me | —CHMeCH$_2$Me | —(CH$_2$)$_3$—Me |
| —CHMeCH$_2$Me | —Me | —CHMeCH$_2$Me | —Me | —CH$_2$Me | —Me |
| —CHMeCH$_2$Me | —Me | —CHMeCH$_2$Me | —Me | —(CH$_2$)$_2$—Me | —Me |
| -cyclohexyl | —Me | -cyclohexyl | —Me | -cyclohexyl | —Me |
| —CH$_2$CHMe$_2$ | -cyclohexyl | —CH$_2$CHMe$_2$ | —Me | —CH$_2$CHMe$_2$ | -cyclohexyl |
| —CH$_2$CHMe$_2$ | -cyclohexyl | —CH$_2$CHMe$_2$ | —Me | —CH$_2$CHMe$_2$ | —Me |
| —CHMeCH$_2$Me | —CHMe$_2$ | —CHMeCH$_2$Me | —CHMe$_2$ | —CHMeCH$_2$Me | —Me |
| —CH$_2$-Phe | —Me | —CH$_2$-Phe | —Me | —CH$_2$-Phe | —Me |
| -cyclohexyl | —Me | -cyclohexyl | —Me | -cyclohexyl | —Me |
| —CHMe$_2$ | —CHMe$_2$ | —CHMe$_2$ | —Me | —CHMe$_2$ | —Me |
| —CHMe$_2$ | —CHMe$_2$ | —CHMe$_2$ | —CHMe$_2$ | —CHMe$_2$ | —Me |
| —CH$_2$—Me | —CHMe$_2$ | —CH$_2$Me | —Me | —CH$_2$—Me | —Me |
| —CH$_2$—Me | —CHMe$_2$ | —CH$_2$Me | —CHMe$_2$ | —CH$_2$—Me | —Me |
| —(CH$_2$)$_2$—Me | —CHMe$_2$ | —(CH$_2$)$_2$—Me | —Me | —(CH$_2$)$_2$—Me | —Me |
| —(CH$_2$)$_2$—Me | —CHMe$_2$ | —(CH$_2$)$_2$—Me | —CHMe$_2$ | —(CH$_2$)$_2$—Me | —Me |
| —(CH$_2$)$_3$—Me | —CHMe$_2$ | —(CH$_2$)$_3$—Me | —Me | —(CH$_2$)$_3$—Me | —Me |
| —(CH$_2$)$_3$—Me | —CHMe$_2$ | —(CH$_2$)$_3$—Me | —CHMe$_2$ | —(CH$_2$)$_3$—Me | —Me |
| —CH$_2$—CH=CH$_2$ | —CHMe$_2$ | —CH$_2$—CH=CH$_2$ | —Me | —CH$_2$—CH=CH$_2$ | —Me |
| —CH$_2$—CH=CH$_2$ | —CHMe$_2$ | —CH$_2$—CH=CH$_2$ | —CHMe$_2$ | —CH$_2$—CH=CH$_2$ | —Me |

Me = methyl; Phe = phenyl

Suitable coupling reagents for carrying out process 3b are all those which are suitable for establishing an amide bond (cf. for example: Houben-Weyl, Methoden der organischen Chemie [Methods in Organic Chemistry], Volume 15/2; Bodanszky et al., Peptide Synthesis 2nd ed. (Wiley & Sons, New York 1976) or Gross, Meienhofer, The Peptides: Analysis synthesis, biology (Academic Press, New York 1979). The following methods are preferably employed: active ester method using pentachloro- (Pcp) and pentafluorophenol (Pfp), N-hydroxysuccinimide, N-hydroxy-5-norbornene-2,3-dicarboxamide (HONB), 1-hydroxybenzotriazole (HOBt) or 3-hydroxy-4-oxo-3,4-dihydro-1,2,3-benzotriazine as alcohol component, coupling with carbodiimides such as dicyclohexylcarbodiimide (DCC) by the DCC additive process, or using n-propanephosphonic anhydride (PPA) and the mixed anhydride method using pivaloyl chloride, ethyl chloroformate (EEDQ) and isobutyl chloroformate (IIDQ), or coupling benzotriazol-1-yl)-1,1,3,3,-tetramethyluronium tetrafluoroborate (TBTU).

Coupling with phosphonium reagents, such as bis(2-oxo-3-oxazolidinyl)-phosphonium acid chloride (BOP-Cl), benzotriazol-1-yl-oxy-tris(dimethylamino-phosphonium) hexafluorophosphate (BOP) and phosphonic ester reagents, such as diethyl cyanophosphonate (DEPC) or diphenylphosphoryl azide (DPPA), is preferred.

Basic reaction auxiliaries which are employed for carrying out process 3b are the tertiary amines mentioned under process 3a, in particular trialkylamines, such as triethylamine, N,N-diisopropylethylamine or N-methylmorpholine.

Diluents which are employed for carrying out process 3b are the halogenated hydrocarbons mentioned under process 3a, in particular chlorohydrocarbons.

Process 3b is carried out by combining compounds of the formula (IId) in a diluent under high-dilution conditions in the presence of one of the abovementioned coupling reagents and in the presence of a basic reaction auxiliary and stirring the mixture. The reaction time is 4 to 72 hours. The reaction is carried out at temperatures between −5° C. and +100° C., preferably between −5° C. and +50° C., particularly preferably at 0° C. to room temperature. The process is carried out under atmospheric pressure.

To carry out process 3b according to the invention, 1.0 to 3.0 mol, preferably 1.0 to 1.5 mol, of coupling reagent are generally employed per mole of N-methyl-L-isoleucyl-D-lactyl-N-methyl-L-isoleucyl-D-lactyl-N-methyl-L-isoleucyl-D-lactic acid of the formula (IId).

When the reaction is complete, the reaction solution is washed until weakly alkaline, and the organic phase is separated off, dried and concentrated in vacuo. The products obtained can be purified in the customary manner by recrystallization, distillation in vacuo or by column chromatography (cf. also the preparation examples).

Using processes 3a and 3b according to the invention, open-chain hexadepsipeptides with a depsipeptide sequence constructed in the L- as well as the D-configuration give cyclohexadepsipeptides (enniatins) while maintaining the original configuration of the starting substances.

The depsipeptides according to the invention which are used as starting compounds can be prepared by processes known per se, for example the process described by H.-G. Lerchen and H. Kunz (Tetrahedron Lett. 26 (43) (1985) pp. 5257–5260; 28 (17) (1987) pp. 1873–1876) exploiting the esterification method described by B. F. Gisin (Helv. Chim. Acta 56 (1973) p. 1476).

The N-methyl-amino acids and 2-halocarboxylic acid derivatives used as starting materials are known in some cases (cf. for example: N-methyl-amino acids: R. Bowmann et al. J. Chem. Soc. (1950) p. 1346; J. R. McDermott et al. Can. J. Chem. 51 (1973) p. 1915; H. Wurziger et al., Kontakte [Catalysts] (Merck.Darmstadt) 3 (1987) p. 8; 2-halocarboxylic acid derivatives: S. M. Birnbaum et al. J. Amer. Chem. Soc. 76 (1954) p. 6054, C. S. Rondestvedt, Jr. et al. Org. Reactions 11 (1960) p. 189 [Review]) or they can be obtained by the processes described in these publications.

The coupling reagents which are used for the coupling reaction to synthesize the depsipeptides (II), (III), (IV), (V) and (VI) according to the invention which are employed as starting compounds are those mentioned under process 3b.

The open-chain hexadepsipeptides (II) in accordance with the invention can thus be obtained by a process which embraces the following subsequence steps:
a) Synthesis of the didepsipeptides of the formulae (IV) to (VI) by processes 9, 11 and 13:

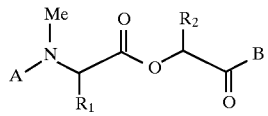
(IV)

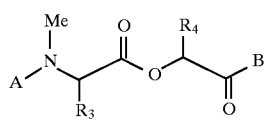
(V)

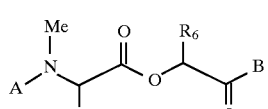
(VI)

in which A is a n N-terminal protecting group, such as, for example, the benzyl or benzyloxycarbonyl group, and B is a C-terminal protecting group, such as, for example, the tert-butoxy group.

In the case of formula (VI), this corresponds to the following equation:

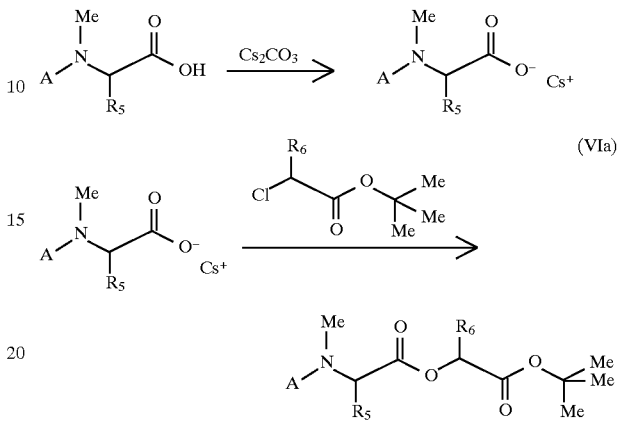
(VIa)

If appropriate, the enantiomerically pure compounds of the formulae (IV), (V) and (VI) according to the invention can also be prepared via separation of the diastereomers by customary methods, such as, for example, crystallizaiton, by column chromatography or by counter-current distribution. A decision about the optimal process will have to be made in each individual case, and sometimes it is also expedient to combine individual processes.

At the end of this stage, it is either possible to eliminate the N-terminal protecting group from the derivatives of the formula (VIa) in a manner known per se, for example by catalytic hydrogenation, to prepare the derivatives of the formula (VIb), or to eliminate the C-terminal protecting group from the derivatives of the formula (IV) and (V) in a manner known per se, preferably acidolysis, to synthesize the derivatives (IVb) and (Vb):

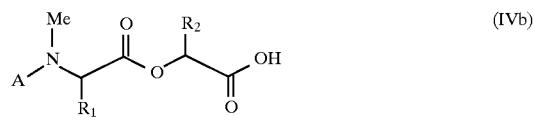
(IVb)

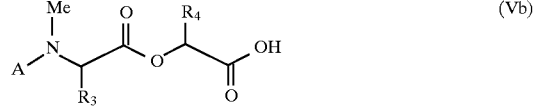
(Vb)

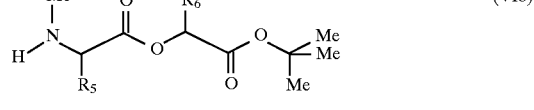
(VIb)

b) Synthesis of the tetradepsipeptides of the formula

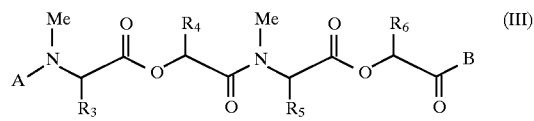
(III)

by the following equation in accordance with process 7:

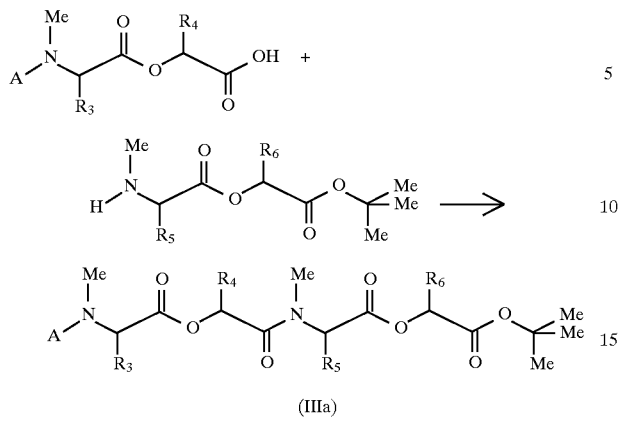

(IIIa)

The N-terminal protecting group can subsequently be eliminated from the derivatives of the formula (IIIa), for example by catalytic hydrogenation as indicated above, to prepare the derivatives of the formula

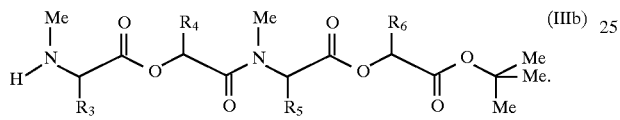

(IIIb)

c) Synthesis of the open-chain hexadepsipeptides of the formula

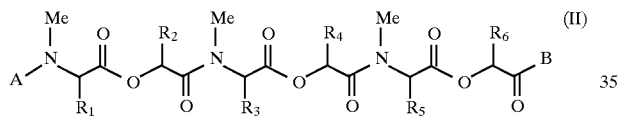

(II)

by the following equation in accordance with process 5:

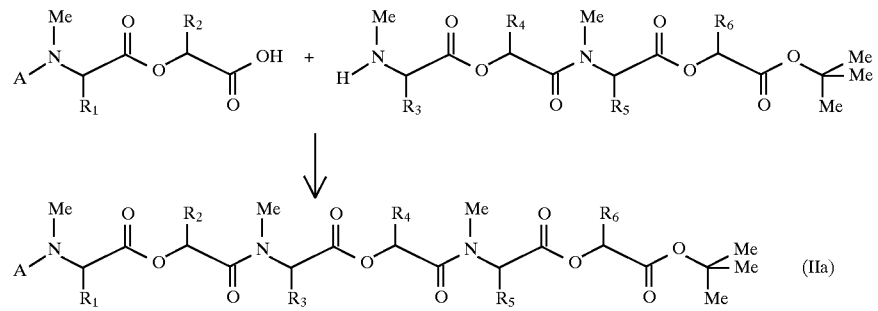

(IIa)

The C-terminal protecting group can subsequently be eliminated from the derivatives of the formula (IIa) in a manner known per se, for example by acidolysis as indicated above, to prepare the derivatives of the formula:

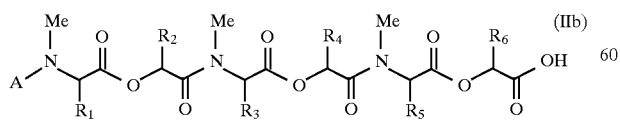

(IIb)

At the end of this step, the carboxyl-activated derivatives of the open-chain hexadepsipeptides can be synthesized, for example the pentafluorophenyl ester of the formula

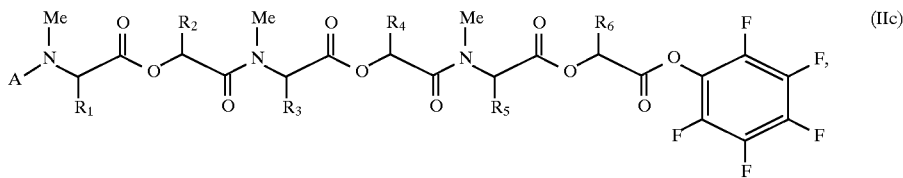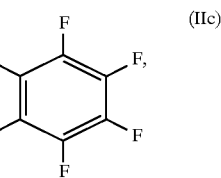

or the N-terminal protecting group is eliminated from the derivatives of the formula (IIb) in a manner known per se, for example by catalytic hydrogenation as indicated above, to prepare the derivatives of the formula

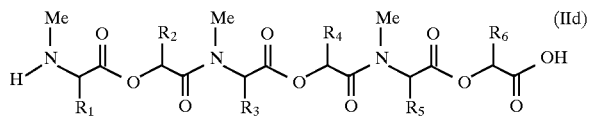

The products obtained can be purified in a customary manner by recrystallization, distillation in vacuo or by column chromatography (cf. also the preparation examples).

While having low toxicity to warm-blooded species, the active compounds are suitable for combating pathogenic endoparasites which occur in humans and in animal keeping and livestock breeding in productive livestock, breeding animals, zoo animals, laboratory animals, experimental animals and pets. In this context, they are active against all or individual stages of development of the pests and against resistant and normally-sensitive species. By combating the pathogenic endoparasites, it is intended to reduce disease, deaths and decreases in performance (for example in the production of meat, milk, wool, hides, eggs, honey etc.), so that more economical and simpler animal keeping is possible by using the active compounds. The pathogenic endoparasites include cestodes, trematodes, nematodes and Acantocephala, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonismus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp., Arisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example: Filicollis spp., Moniliformis spp., Macracanthorhynchus spp., Prosthenorchis spp.

The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carps, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically.

The active compounds are administered directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, tablets, capsules, passes, drinks, granules, or solutions, suspensions and emulsions which can be administered orally, or boli, medicated feed or drinking water. Dermal administration is effected, for example, in the form of dipping, spraying or pouring-on and spotting-on. Parenteral administration is effected, for example, in the form of an injection (intramuscular, subcutaneous, intravenous, intraperitoneal) or by implants.

Suitable preparations are:

Solutions such as injectable solutions, oral solutions, concentrates for oral administration after dilution, solutions for use on the skin or in body cavities, pour-on and spot-on formulations, gels;

Emulsions and suspensions for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injectable solutions are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and packaged.

The following may be mentioned as solvents: physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the injectable solutions, it being possible to dispense with working under sterile conditions.

Solutions for use on the skin are applied dropwise, brushed on, rubbed in, splashed on or sprayed on. These solutions are prepared as described above in the case of injectable solutions.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and methacrylates.

Gels are applied to, or brushed onto, the skin, or introduced into body cavities. Gels are prepared by treating solutions which have been prepared as described in the case of the injectable solutions with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other adjuvants such as colourants, absorption accelerators, antioxidants, light stabilizers and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol monobutyl ether, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-oxy-methylene-1,3-dioxolane.

Colourants are all colourants which are licensed for use on animals and can be in the dissolved or suspended state.

Examples of absorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenising this phase with the solvent of the other phase, with the aid of suitable emulsifiers and, if appropriate, other adjuvants such as colourants, absorption accelerators, preservatives, antioxidants, light stabilizers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as synthetic duck preen fat, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

Ampholytic surfactants such as disodium N-lauryl-β-iminodipropionate or lecithin;

Anionic surfactants such as sodium lauryl sulphate, fatty alcohol ether sulphates, the monoethynolamine salt of mono/dialkyl polyglycol ether orthophosphoric esters;

The following may be mentioned as other adjuvants: viscosity-increasing substances and substances which stabilize the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of an injection. They are prepared by suspending the active compound in an excipient liquid, if appropriate with the addition of further adjuvants such as wetting agents, colourants, absorption accelerators, preservatives, antioxidants light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, carcass meals, cereal meals and coarse cereal meals, and starches.

Adjuvants are preservatives, antioxidants and colourants which have already been indicated further above.

Other suitable adjuvants are lubricants and glidants such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazothiazole, benzimidazole carbamates, praziquantel, pyrantel, febantel.

Ready-to-use preparations contain the active compound in concentrations of 10 ppm–20% by weight, preferably 0.1–10% by weight.

Preparations which are diluted prior to administration contain the active compound in concentrations of 0.5–90% by weight, preferably 5–50% by weight.

In general, it has proved advantageous to administer amounts of approximately 1 to approximately 100 mg of active compound per kg of body weight per day, to achieve effective results.

FORMULATION EXAMPLES

Example 1

200 g of water for injection are treated in nitrogen gas for 10 minutes. 0.3 g of ascorbic acid and 43.2 g of glucose are dissolved in this amount of water and 3.55 g of 0.5 M-arginine solution are then added to adjust the pH. 0.15 g of enniatin A and 24 g of ultra pure egg phospholipid (for example Pipoid E PC) are dispersed in this medium, and the mixture is made up to 300 g with nitrogen-treated water (active compound: phospholipid ratio=1:160).

This dispersion is prehomogenized for 30 minutes at 75° C. using a rapid mixer (for example Ultra-Turrax), under nitrogen protection. The predispersion is filtered through a 5 µm filter.

The predispersion is subsequently homogenized for one hour at 75° C., 800 bar and under nitrogen protection using an non-abrasive high-pressure jet homogenizer. After cooling to room temperature, the mixture is subjected to a decontamination filtration step (0.2 µm). The content is 100% of the nominal content.

15.3 ml aliquots of the dispersion are packaged into 250 or 50 ml bottles and frozen with the aid of the spin- or shell-freezing method at −65° C. (cooling mixture of dry ice/ethanol) to give a thin product cake.

The frozen product is placed on the shelves of a lyophilizer which have been precooled to −50° C. and dried for 14 hours at −30° C. and 0.05 mbar. Final drying is carried out for 7 hours at 30° C. and 0.001 mbar. The lyophilizer is reconstituted using glucose solution or water. The content is 100% of the nominal content.

| | Liposome characteristics: | |
| --- | --- | --- |
| | prior to lyophilization | after lyophilization |
| mean size | 49 nm | 53 nm |
| dispersivity index K2 | 0.275 | 0.379 |
| turbidity | 315 units | 401 units |
| osmolarity | 1.24 osmol | 1.25 mosmol |
| pH | 6.3 | 6.5 |

Example 2

200 g of water for injection are treated with nitrogen gas for 10 minutes. 0.3 g of ascorbic acid and 43.2 g of glucose are dissolved in this amount of water and 3.55 g of 0.5 M-arginine solution are then added to adjust the pH. 0.15 g of enniatin A and 30 g of ultra pure soya bean phospholipid (for example Phospholipon 90) are dispersed in this medium, and the mixture is made up to 300 g with nitrogen-treated water (active compound: phospholipid ratio=1:200).

This dispersion is prehomogenized for 30 minutes at 75° C. using a rapid mixer (for example Ultra-Turrax), under nitrogen protection. The predispersion is filtered through a 5 µm filter.

The predispersion is subsequently homogenized for one hour at 75° C., 800 bar and under nitrogen protection using a non-abrasive high-pressure jet homogenizer. After cooling to room temperature, the mixture is subjected to a decontamination filtration step (0.2 µm). The content is 100% of the nominal content.

In contrast to Example 1, the dispersion is packaged into suitable bottles, but frozen at −65° C., but without using the spin- or shell-freezing method.

The product is dried for 7 hours at +30° C. and 0.05 mbar (main drying step) and subjected to a final drying step at +30° C. and 0.001 mbar.

The liposome properties of Example 1 are retained.

Example 3

200 g of water suitable for injection are treated with nitrogen gas for 10 minutes. 0.3 g of ascorbic acid and 43.2 g of glucose are dissolved in this amount of water and 3.55 g of 0.5 M-arginine solution are then added to adjust the pH. 0.24 g of enniatin A and 22.6 g of ultra pure, saturated phospholipid (for example Epikuron 200 SH) and 2.4 g of synthetic DMPG-Na are dispersed in this medium, and the mixture is made up to 300 g with nitrogen-treated water (active compound: phospholipid ratio=1:100).

This dispersion is prehomogenized for 30 minutes at 75° C. using a rapid mixer (for example Ultra-Turrax), under nitrogen protection. The predispersion is filtered through a 5 μm filter.

The predispersion is subsequently homogenized for one hour at 75° C., 800 bar and under nitrogen protection using an non-abrasive high-pressure jet homogenizer. After cooling to room temperature, the mixture is subjected to a decontamination filtration step (0.2 μm). The content is 100% of the nominal content.

15.3 ml aliquots of the dispersion are packaged into 250 or 50 ml bottles and frozen at −65° C. (cooling mixture of dry ice/ethanol) with the aid of the spin- or shell-freezing method to give a thin product cake.

The frozen product is placed onto the shelves of a lyophilizer which have been precooled to −50° C. and dried for 14 hours at −30° C. and 0.05 mbar. The product is then subjected to a final drying step for 7 hours at 30° C. and 0.001 mbar.

The lyophilizate is reconstituted using glucose solution or water. The content is 100% of the nominal content.

Example A
*Trichinella spiralis* in vitro

*Trichina lavae* are isolated from mice's muscle and washed in 0.9% NaCl supplemented with 20 μg/ml sisomycin and 2 μg/ml clotrimazole. The actual incubation of approximately 20 trichinae per measurement is carried out in 2 ml of a solution composed of 10 g of Bacto Casitone, 5 g of yeast (yeast extract), 2.5 g of glucose, 0.4 g of $KH_2PO_4$ and 0.4 g of $K_2HPO_4$ per 500 ml, pH 7.2, containing 10 μm/ml of sisomycin and 1 μm/ml of clotrimazole. 10 mg of the substance to be tested are dissolved in 0.5 ml of DMSO, and such an amount is added to the incubation medium that the end concentration is 100, 10 and 1 μm/ml. The experiment is evaluated after incubation for 5 days at 19° C.

Enniatins $A_1$, B and $B_1$ are effective at concentration of 100 μm/ml.

Example B

Female Heterakis spumose nematodes are isolated from the colon and caecum of mice. 10 females are incubated for 3 days at 37° C. in 1.5 ml of medium used for the *Trichinella spiarlis* in-vitro test. The addition of test substances is likewise carried out as described for the trichina test. To test the anthelmintic activity, mobility and egg excretion are assessed in comparison with the control. Enniatins $A_1$, B and $B_1$ are active at a concentration of 10 μM/ml.

Example C
In vivo nematode test
*Haemonchus contortus*/sheep

Shaft which have been infected experimentally with *Haemonchus contortus* were treated after the prepatent time of the parasite had elapsed. The active compounds were applied orally and/or intravenously in the form of the pure active compound.

The degree of effectiveness is determined by quantitatively counting the worm eggs excreted with the faeces before and after the treatment.

If the egg excretion has stopped completely after the treatment, this means that the worms were aborted or are damaged to such an extent that they no longer produce eggs (dosis effectiva).

Active compounds tested and effective dosage rates (dosis effectiva) can be seen from the table which follows:

| Active compound Example No. | Dosis effectiva in mg/kg |
| --- | --- |
| 1 | 5 |
| 2 | 5 |
| 4 | 5 |
| 5 | 5 |

Preparation Examples

Example 1

Cyclo(N-methyl-L-isoleucyl-D-lactyl-N-methyl-L-isoleucyl-D-lactyl-N-methyl-L-isoleucyl-D-lactyl-)

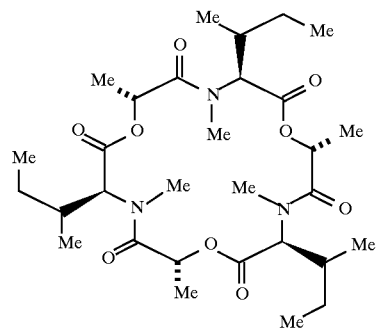

At an internal temperature of 95° C., 0.99 g (1.08 mmol) of Z-(L-MeIle-D-Lac-)$_3$-O-Pfp in 50 ml of absolute dioxane are injected uniformly in the course of 6 hours into a rapidly stirred suspension of 1.5 g of 10% strength palladium/charcoal in 550 ml of absolute dioxane containing 12 ml of ethanol and 160 mg (1.08 mmol) of 4-pyrrolidino-pyridine. During this process, hydrogen is passed through the reaction solution. The mixture is subsequently stirred for a further 4 hours at 95° C. and for 12 hours at room temperature. The entire reaction batch is filtered and concentrated in vacuo. The colorless oily residue is taken up in chloroform and washed twice using 5% strength citric acid, twice using $NaHCO_3$ solution and twice using water. The organic phase is dried over sodium sulphate, and the solvent is subsequently distilled off in vacuo. The crude product which remains can be prepurified chromatographically over a silica gel column (silica 60-Merck, particle size:0.04 to 0.063 mm) using the eluent toluene/ethyl acetate (4:1) (purity 84%). This is followed by purification by means of preparative HPLC. 710 mg (36.8% of theory) of cyclo(-N-methyl-L- isoleucyl-D-lactyl-N-methyl-L-isoleucyl-D-lactyl-N-methyl-L-isoleucyl-D-lactyl-) are obtained.

M.p.: 210°–212° C.

$^1$H NMR (400 MHz, CDCl$_3$, δ): 0.87 (t, 9H, —CH$_2$—C<u>H</u>$_3$; J=7.3 Hz); 0.98; 1.44 (2d, 18H, —CH—C<u>H</u>$_3$; J=6.5 Hz); 1.35–1.41 (br. m, 3H, —C<u>H</u>—CH$_3$); 2.02–2.04(br.m, 6H, —C<u>H</u>$_2$—CH$_3$); 3.03 (s, 9H, —N—C<u>H</u>$_3$); 4.45 (m, 3H, N—C<u>H</u>—CO); 5.57–5.62 (m, 3H, O—C<u>H</u>—CO) ppm $^{13}$C NMR (100 MHz, CDCl$_3$, δ): 10.9; 16.0; 16.6 (—<u>C</u>H$_3$); 24.8 (—<u>C</u>H$_2$—); 33.3 (—<u>C</u>H—); 33.9 (—N—<u>C</u>H$_3$); 61.9 (—N—<u>C</u>H—); 66.4 (—O—<u>C</u>H—); 169.3 (—<u>C</u>O—N—); 169.9 (—<u>C</u>O—O—) ppm FAB MS m/z (%): 598 (M$^+$+H,12); 597 (37); 541 (42); 524 (14); 182 (100)

The compounds of the formula (I) listed in Table 1 below can be prepared analogously in the form of the LDLDLD stereoisomers.

TABLE 1

Examples of compounds of the general formula (I)

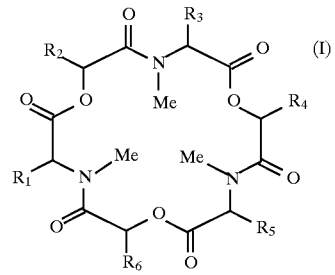

| Ex. No. | R$^1$ | R$^2$ | R$^3$ | R$^4$ | R$^5$ | R$^6$ | Physical Data[a] |
|---|---|---|---|---|---|---|---|
| 2 | —CH$_2$CHMe$_2$ | —Me | —CH$_2$CHMe$_2$ | —Me | —CH$_2$CHMe$_2$ | —Me | 16.5; 21.9; 22.8 (—<u>C</u>H$_3$); 24.9 (—<u>C</u>H—); 32.0 (—N—<u>C</u>H$_3$); 37.4 (—<u>C</u>H$_2$—); 55.8 (—N—<u>C</u>H—); 67.0 (—O—<u>C</u>H—); 169.4 (—<u>C</u>O—N—); 170.5 (—<u>C</u>O—O—) |
| 3 | —CH$_2$CHMe$_2$ | —Me | —CH$_2$CHMe$_2$ | —CH$_2$—Ph | —CH$_2$CHMe$_2$ | —Me | 16.3; 16.4; 21.7; 21.8; 22.8; 22.9; 23.0 (—<u>C</u>H$_3$); 24.6; 24.9 (—<u>C</u>H—); 31.0; 31.7; 32.8 (—N—<u>C</u>H$_3$); 36.8; 37.4; 37.6 (—<u>C</u>H$_2$—); 54.6; 553; 56.5 (—N—<u>C</u>H—); 67.0; 67.1; 70.2 (—O—<u>C</u>H—); 168.8; 169.7 (—<u>C</u>O—N—); 170.3; 170.6; 170.6 (—<u>C</u>O—O—). |
| 4 | —CHMeCH$_2$Me | —CHMe$_2$ | —CHMeCH$_2$Me | —CHMe$_2$ | —CH$_2$—Ph | —CHMe$_2$ | 10.6; 15.7; 15.9; 18.2; 18.3 (—<u>C</u>H$_3$); 18.3; 18.6; 19.0; 25.0 (—<u>C</u>H$_2$—); 25.2; 29.4; 29.7; 30.3 (—<u>C</u>H—); 31.4; 31.8; 36.0 (—N—<u>C</u>H$_3$); 35.0 (—<u>C</u>H$_2$—Ph); 59.6; 60.5; 62.6 (—N—<u>C</u>H—); 74.8; 75.2 (—O—<u>C</u>H—); 126.6; 128.4; 129.1 (aromatic —<u>C</u>H); 137.7 (aromatic —<u>C</u>); 169.1; 1692; 169.7; (—<u>C</u>O—N—); 169.3; 170.3; 170.4 (—<u>C</u>O—O—) |
| 5 | —CHMeCH$_2$Me | —CHMe$_2$ | —CHMeCH$_2$Me | —Me | —CHMeCH$_2$Me | —Me | 10.3; 10.6; 11.4; 15.3; 15.8; 16.0; 16.7; 16.8; 18.0; 18.4 (—<u>C</u>H$_3$); 24.4; 24.9; 25.0 (—<u>C</u>H$_2$); 29.9; 32.3; 34.1; 34.7 (—<u>C</u>H—); 31.2; 31.6; 35.6 (N—<u>C</u>H$_3$); 59.5; 60.5; 65.1 (N—<u>C</u>H—); 66.1; 67.5; 74.0 (O—<u>C</u>H—); 169.0; 169.1; 169.2; (<u>C</u>O—N); 169.8; 170.1; 170.6 (—<u>C</u>O—O) |
| 6 | —CH$_2$CHMe$_2$ | —Me | —CHMeCH$_2$Me | —Me | —CHMeCH$_2$Me | —Me | 10.6; 10.9; 15.7; 16.2; 16.5; 17.0; 21.8; 22.9; (—<u>C</u>H$_3$); 24.4; 37.1 (—<u>C</u>H$_2$—); 24.8; 33.3; 34.3; (—<u>C</u>H—); 31.0; 32.7; 33.0; (—N—<u>C</u>H$_3$); 57.0; 60.0; 62.0; (—N—<u>C</u>H—); 66.1; 66.6; 67.4; (—O—<u>C</u>H—); 168.9; 169.3; 169.5; (—<u>C</u>O—N—); 170.0; 170.5 (—<u>C</u>O—O) |

[a] $^{13}$C—NMR (100 MHz, CDCl$_3$, δ)

Starting Substances of the formula (II)

Example (II-1)

tert-Butyl N-benzyloxycarbonyl-N-methyl-L-isoleucyl-D-lactyl-N-methyl-L-isoleucyl-D-lactyl-N-methyl-L-iso-leucyl-D-lactate

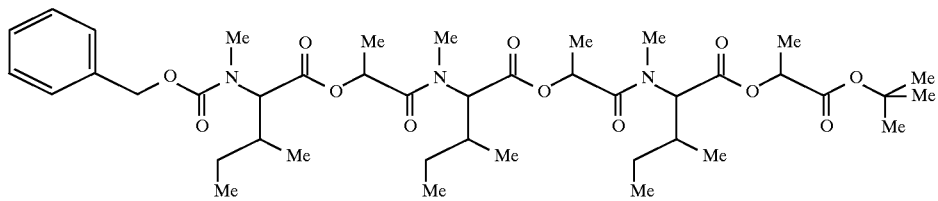

4.7 g (36.3 mmol) of N,N-diisopropylethylamine ("Hünig's Base") and 4.6 g (18.1 mmol) of bis(2-oxo-3-oxazolidinyl)phosphonium acid chloride (BOP-Cl) are added at 0° C. to a solution of 5.8 g (16.5 mmol) of Z-L-MeIle-D-Lac-OH and 7.8 g (16.5 nmol) of H-(-L-MeIle-D-Lac-)$_2$-O-$^t$Bu in 150 ml of methylene chloride, and the mixture is stirred for 4 hours. The reaction solution is shaken twice with water, and the organic phase is separated off and, after drying over sodium sulphate, concentrated in vacuo. The crude product which remains is chromatographed over a silica gel column (silica gel 60-Merck, particle size: 0.04 to 0.063 mm) using the eluent toluene-:ethyl acetate (5:1). 10.3 g (77.4% of theory) of tert-butyl N-benzyloxycarbonyl-N-methyl-L-isoleucyl-D-lactyl-N-methyl-L-isoleucyl-D-lactyl-N-methyl-L-isoleucyl-D-lactate are obtained.

FAB MS m/z (%): 805 (M$^+$,3); 749 (M$^+$—H$_2$C=CMe$_2$, 10); 732 (9); 793 (10); 91 (100)

Example (II-2)

N-Benzyloxycarbonyl-N-methyl-L-isoleucyl-D-lactyl-N-methyl-L-isoleucyl-D-lactyl-N-methyl-L-isoleucyl-D-lactic acid

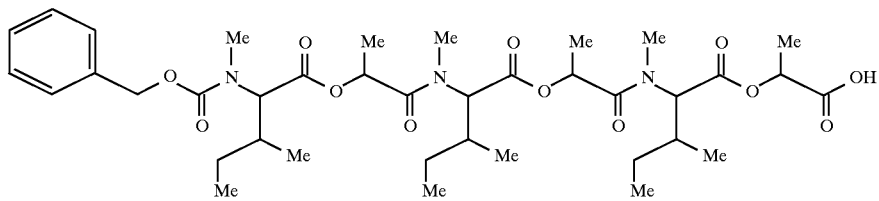

Dry hydrogen chloride gas is passed for 20 minutes into a solution, cooled to 0° C., of 9.2 g (11.2 mmol) of Z-(L-MeIle-D-Lac-)$_3$-O-$^t$Bu in 150 ml of absolute methylene chloride. The mixture is subsequently stirred for approximately 16 hours at room temperature, and the entire reaction batch is concentrated in vacuo. 7.1 g (82.9% of theory) of N-benzyloxy-carbonyl-N-methyl-L-isoleucyl-D-lactyl-N-methyl-L-isoleucyl-D-lactyl-N-methyl-L-isoleucyl-D-lactic acid, which can be reacted further without further purification, are obtained.

MS m/z (%): 749 (M$^+$,10); 721 (1); 693 (2); 533 (0.5); 91 (100)

Example (II-3)

Pentafluorophenyl N-benzyloxycarbonyl-N-methyl-L-isoleucyl-D-lactyl-N-methyl-L-isoleucyl-D-lactyl-N-methyl-L-isoleucyl-D-lactate

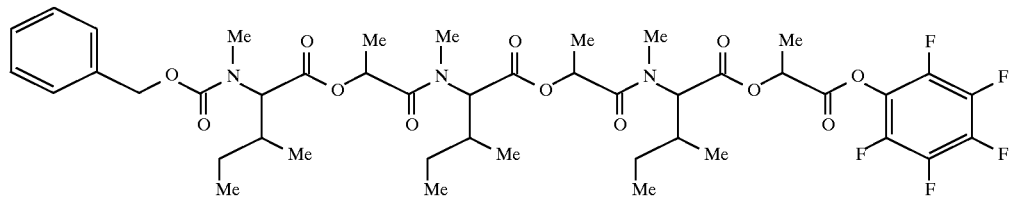

5.0 g (6.67 mmol) of Z-(L-MeIle-D-Lac)$_3$-OH together with 1.23 g (6.67 mmol) of pentafluorophenol are dissolved in 125 ml of absolute ethyl acetate (inert gas atmosphere). 1.38 g (6.67 mmol) of dicyclohexylcarbodiimide (DCC) are added at 0° C., and stirring is continued for 4 hours at this temperature. After precipitated dicyclohexylurea has been filtered off, the filtrate is concentrated to dryness in vacuo, and the residue is chromatographed over a pre-dried silica gel column (silica gel 60-Merck, particle size: 0.04 to 0.063 mm) using the eluent toluene:ethyl acetate (10:1).

3.3 g (54% of theory) of pentafluorophenyl N-benzyloxycarbonyl-N-methyl-L-isoleucyl-D-lactyl-N-methyl-L-isoleucyl-D-lactyl-N-methyl-L-isoleucyl-D-lactate are obtained as a colourless oil.

FAB MS m/z (%): 915 (M$^+$,2); 914 (M$^+$–H,4); 859 (9); 814 (1); 780 (5); 91 (100)

Example (II-4)

N-Methyl-L-isoleucyl-D-lactyl-N-methyl-L-isoleucyl-D-lactyl-N-methyl-L-isoleucyl-D-lactic acid

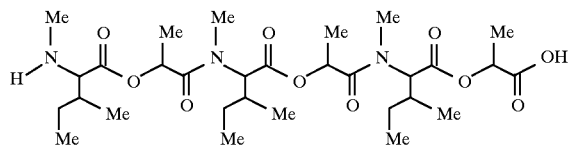

1.0 g (1.33 mmol) of Z-(L-MeIle-D-Lac)$_3$-OH is hydrogenated in 20 ml of ethanol in the presence of 0.15 g of Pd(OH)$_2$/charcoal [Pd content 20%] until the uptake of hydrogen has ceased (approximately 2 hours). After the catalyst has been filtered off, the entire reaction solution is concentrated in vacuo. 0.81 g (100% of theory) of N-methyl-L-isoleucyl-D-lactyl-N-methyl-L-isoleucyl-D-lactyl-N-methyl-L-isoleucyl-D-lactic acid is obtained and can be cyclized without further purification.

EI MS m/z (%): 615 (M$^+$,3); 600 (1); 558 (7); 472 (8); 386 (14); 100 (100)

The compounds of the general formula (II) which are listed in Table 2 below can be prepared analogously in the form of the LDLDLD stereoisomers.

TABLE 2

Examples of compound of the formula (II)

$$\text{Me-N(A)-CH(R}^1\text{)-C(O)-O-CH(R}^2\text{)-C(O)-N(Me)-CH(R}^3\text{)-C(O)-O-CH(R}^4\text{)-C(O)-N(Me)-CH(R}^5\text{)-C(O)-O-CH(R}^6\text{)-C(O)-B} \quad (II)$$

| Ex. No. | A | $R^1$ | $R^2$ | $R^3$ | $R^4$ | $R^5$ | $R^6$ | B | Physical Data[a] |
|---|---|---|---|---|---|---|---|---|---|
| II-5 | —CO—O—CH$_2$Ph | —CH$_2$CHMe$_2$ | —Me | —CH$_2$CHMe$_2$ | —Me | —CH$_2$CHMe$_2$ | —Me | —O—C$_6$F$_5$ | 915 (M$^+$,4); 860 (8); 780 (3); 91 (100) |
| II-6 | —CO—O—CH$_2$Ph | —CH$_2$CHMe$_2$ | —Me | —CH$_2$CHMe$_2$ | —Me | —CH$_2$CHMe$_2$ | —Me | —OH | 750 (M$^+$+H); 706 (2); 461 (8); 91 (100) |
| II-7 | —CO—O—CH$_2$Ph | —CH$_2$CHMe$_2$ | —Me | —CH$_2$CHMe$_2$ | —Me | —CH$_2$CHMe$_2$ | —Me | —OCMe$_3$ | 805 (M$^+$,1); 749 (M$^+$—H$_2$C=CMe$_2$ 12); 91 (100) |
| II-8 | —CO—O—CH$_2$Ph | —CH$_2$CHMe$_2$ | —Me | —CH$_2$Ph | —Me | —CH$_2$CHMe$_2$ | —Me | —O—C$_6$F$_5$ | 992 (M$^+$+H,1); 609 (2); 514 (13); 91 (100) |
| II-9 | —CO—O—CH$_2$Ph | —CH$_2$CHMe$_2$ | —Me | —CH$_2$Ph | —Me | —CH$_2$CHMe$_2$ | —Me | —OH | 826 (M$^+$,4); 769 (22); 690 (10); 91 (100) |
| II-10 | —CO—O—CH$_2$Ph | —CH$_2$CHMe$_2$ | —Me | —CH$_2$Ph | —Me | —CH$_2$CHMe$_2$ | —Me | —O—CMe$_3$ | 881 (M$^+$,4); 825 (M$^+$—H$_2$C=CMe$_2$ 16); 807 (7); 869 (14); 91 (100) |
| II-11 | —CH$_2$Ph | —CHMeCH$_2$Me | —CHMe$_2$ | —CHMeCH$_2$Me | —CHMe$_2$ | —CH$_2$Ph | —CHMe$_2$ | —O—C$_6$F$_5$ | 991 (M$^+$+H,6); 913 (M$^+$—Ph,3) 546 (2); 190 (100) |
| II-12 | —CH$_2$Ph | —CHMeCH$_2$Me | —CHMe$_2$ | —CHMeCH$_2$Me | —CHMe$_2$ | —CH$_2$Ph | —CHMe$_2$ | —OH | 824 (M$^+$,3); 766 (10); 704 (37); 190 (100) |
| II-13 | —CH$_2$Ph | —CHMeCH$_2$Me | —CHMe$_2$ | —CHMeCH$_2$Me | —CHMe$_2$ | —CH$_2$Ph | —CHMe$_2$ | —O—CMe$_3$ | 879 (M$^+$,5); 822 (10;760 (21);704 (14); 191 (100) |
| II-14 | —CO—O—CH$_2$Ph | —CHMeCH$_2$Me | —CHMe$_2$ | —CHMeCH$_2$Me | —CHMe$_2$ | —CH$_2$Ph | —CHMe$_2$ | —O—C$_6$F$_5$ | 1034 (M$^+$+H,3); 589 (0.5); 489 (11); 91 (100) |
| II-15 | —CO—O—CH$_2$Ph | —CHMeCH$_2$Me | —CHMe$_2$ | —CHMeCH$_2$Me | —CHMe$_2$ | —CH$_2$Ph | —CHMe$_2$ | —OH | 867 (M$^+$,8); 811 (12); 732 (10); 210 (100) |
| II-16 | —CO—O—CH$_2$Ph | —CHMeCH$_2$Me | —CHMe$_2$ | —CHMeCH$_2$Me | —CHMe$_2$ | —CH$_2$Ph | —CHMe$_2$ | —O—CMe$_3$ | 923 (M$^+$,1); 868 (8); 851 (6); 91 (100) |
| II-17 | —H | —CH$_2$CHMe$_2$ | —Me | —CHMeCH$_2$Me | —Me | —CHMeCH$_2$Me | —Me | —OH | 615 (M$^+$,5); 472 (5); 386 (17); 327 (7); 100 (100) |
| II-18 | —CH$_2$Ph | —CH$_2$CHMe$_2$ | —Me | —CHMeCH$_2$Me | —Me | —CHMeCH$_2$Me | —Me | —O—CMe$_3$ | 761 (M$^+$,1); 688 (M$^+$—OCMe$_3$,4); 642 (5); 586 (5); 190 (100) |
| II-19 | —CH$_2$Ph | —CH$_2$CHMe$_2$ | —Me | —CHMeCH$_2$Me | —Me | —CHMeCH$_2$Me | —Me | —OH | 707 (M$^+$+H, 60); 190 (100) |
| II-20 | —H | —CHMeCH$_2$Me | —CHMe$_2$ | —CHMeCH$_2$Me | —Me | —CHMeCH$_2$Me | —Me | —OH | 790 (M$^+$,1); 789 (M$^+$—H, 1) ; 717 (M$^+$—OCMe$_3$,4); 770 (7); 190 (100) |
| II-21 | —CH$_2$Ph | —CHMeCH$_2$Me | —CHMe$_2$[e] | —CHMeCH$_2$Me | —Me | —CHMeCH$_2$Me | —Me | —OH | |
| II-22 | —CH$_2$Ph | —CHMeCH$_2$Me | —CHMe$_2$ | —CHMeCH$_2$Me | —Me | —CHMeCH$_2$Me | —Me | —O—CMe$_3$ | 796 (M$^+$,2); 795 (M$^+$—H,6); 723 (M$^+$—OCMe$_3$,3); 704 (47); 224 (100) |
| II-23 | —CH$_2$Ph | —CH=Ph | —Me | —CHMeCH$_2$Me | —Me | —CHMeCH$_2$Me | —Me | —O—CMe$_3$ | 705 (M$^+$,2); 632 (M$^+$—OCMe$_3$,7); 614 (26); 558 (39); 269 (100) |
| II-24 | —H | —CH=Ph | —Me | —CHMeCH$_2$Me | —Me | —CHMeCH$_2$Me | —Me | —O—CMe$_3$ | |

[a]FAB MS or EI MS m/z (%)

Starting substances of the formula (III)

Example (III-1)

tert-Butyl N-benzyl-N-methyl-L-leucyl-D-lactyl-N-methyl-L-leucyl-D-lactate

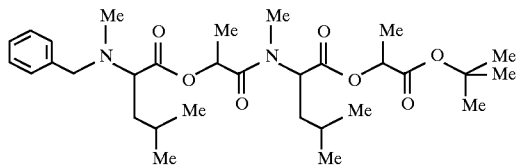

The coupling reaction is carried out analogously to the reaction procedure of Example (II-1) using:
12.4 g (40.3 mmol) of N-benzyl-N-methyl-L-leucyl-D-lactic acid,
11.0 g (40.3 mmol) of tert-butyl N-methyl-L-leucyl-D-lactate,
100 ml of methylene chloride,
11.5 g (88.7 mmol) of N,N-diisopropylethylamine ("Hünig's Base"),
11.3 g (44.3 mmol) of bis(2-oxo-3-oxazolidinyl)-phosphonium acid chloride (BOP-Cl).

The crude product which remains is chromatographed over a silica gel column (silica gel 60-Merck, particle size: 0.04 to 0.063 mm) using the eluent toluene:ethyl acetate (20:1). 21.8 g (96.0% of theory) of tert-butyl N-benzyl-N-methyl-L-leucyl-D-lactyl-N-methyl-L-leucyl-D-lactate are obtained.

EI MS m/z (%): 562 (M$^+$,3); 489 (M$^+$—OCme$_3$,7); 443 (2); 387 (3); 344 (1); 190 (PhCH$_2$—NMe—CH—CH$_2$Me$_2$, 100); 120 (PhCH$_2$—NMe—,31)

Example (III-2)

tert-Butyl N-methyl-L-leucyl-D-lactyl-N-methyl-L-leucyl-D-lactate

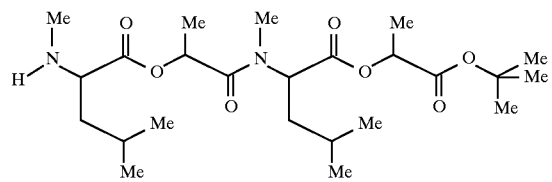

21.8 g (38.7 mmol) of Bn-(-L-MeLeu-D-Lac-)$_2$-O-$^t$Bu are dissolved in 300 ml of ethanol and hydrogenated in the presence of 2.2 g of Pd(OH)$_2$/charcoal [Pd content 20%] until the uptake of hydrogen has ceased (approximately 2.5 hours). After the catalyst has been filtered off, the entire reaction solution is concentrated in vacuo. 18.3 g (100% of theory) of tert-butyl N-methyl-L-leucyl-D-lactyl-N-methyl-L-leucyl-D-lactate are obtained and can be used for the coupling reaction without further purification.

EI MS m/z (%): 472 (M$^+$,4); 457 (1); 428 (1); 399 (6); 100 (HNMe—CH—CH$_2$Me$_2$, 100)

The compounds of the general formula (III) which are listed in Table 3 below can be prepared analogously in the form of the LDLD stereoisomers.

TABLE 3

Examples of compounds of the formula (III)

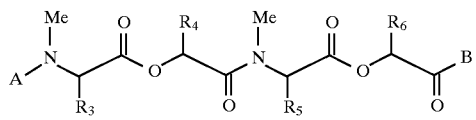

| Ex. No | A | R$^3$ | R$^4$ | R$^5$ | R$^6$ | B | Physical data[a] |
|---|---|---|---|---|---|---|---|
| III-3 | —CH$_2$Ph | —CH$_2$CHMe$_2$ | —CH$_2$Ph | —CH$_2$CHMe$_2$ | —Me | —O—CMe$_3$ | |
| III-4 | —H | —CH$_2$CHMe$_2$ | —CH$_2$Ph | —CH$_2$CHMe$_2$ | —Me | —O—CMe$_3$ | |
| III-5 | —CH$_2$Ph | —CHMeCH$_2$Me | —CHMe$_2$ | —CH$_2$Ph | —CHMe$_2$ | —O—CMe$_3$ | 652 (M$^+$, 8); 595 (M$^+$—CMe$_3$, 14); 579 (M$^+$—OCMe$_3$, 16); 533 (12); 477 (24); 190 (100) |
| III-6 | —H | —CHMeCH$_2$Me | —CHMe$_2$ | —CH$_2$Ph | —CHMe$_2$ | —O—CMe$_3$ | 562 (M$^+$, 2); 518 (2); 489 (M$^+$—OCMe$_3$,4); 363 (7); 100 (100) |
| III-7 | —CH$_2$Ph | —CHMeCH$_2$Me | —Me | —CHMeCH$_2$Me | —Me | —O—CMe$_3$ | 563 (M$^+$+H, 1); 562 (M$^+$, 3); 505 (M$^+$ab,4 CMe$_3$, 7); 489 (M$^+$—OCMe$_3$, 6); 190 (100) |
| III-8 | —H | —CHMeCH$_2$Me | —Me | —CHMeCH$_2$Me | —Me | —O—CMe$_3$ | 472 (M$^+$,1); 359 (11); 273 (6); 100 (100) |

[a]FAB MS or EI MS m/z (%)

Starting substances of the formula (IV), (V) and (VI)

Example (IV-1)

tert-Butyl N-benzyloxycarbonyl-N-methyl-L-leucyl-D-lactate

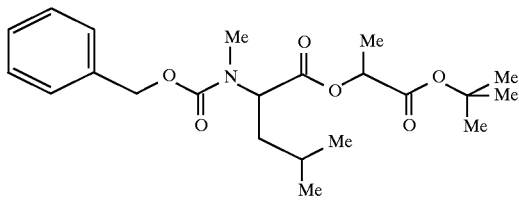

10.0 g (35.8 mmol) of N-benzyloxycarbonyl-N-methyl-leucine are dissolved in 150 ml of methanol and 15 ml of water, 19.5 ml of a 20% strength caesium carbonate solution are added, the mixture is stirred for approximately one hour at room temperature. Then, two portions each of approximately 50 ml of absolute dimethylformamide are added, and the mixture is concentrated in vacuo and dried under a high vacuum. The caesium salt is introduced into 75 ml of dimethylformamide, 7.0 g (35.8 mmol) of tert-butyl L-2-chloro-lactate are added, and the mixture is stirred for approximately 18 hours at room temperature. The entire reaction solution is concentrated in vacuo, the oily residue is taken up in methylene chloride and the mixture is shaken twice with water. The organic phase is then separated off, dried over sodium sulphate and concentrated in vacuo.

The crude product which remains is chromatographed over a silica gel column (silica gel 60-Merck, particle size: 0.04 to 0.063 mm) using the eluent toluene:ethyl acetate (40:1). 14.4 g (100% of theory) of tert-butyl N-benzyloxycarbonyl-N-methyl-L-leucyl-D-lactate are obtained.

EI MS m/z (%): 407 (M$^+$,2); 351 (10); 234 (39); 387 (3); 344 (1); 190 (PhCH$_2$—NMe—CH—CH$_2$Me$_2$,69); 91 (PhCH$_2$, 100)

Example (V-1)

N-Benzyl-N-methyl-L-isoleucyl-D-hydroxyisovaleric acid

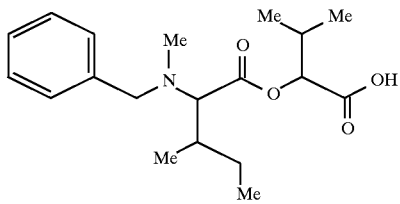

C-terminal acidolysis is carried out analogously to the reaction procedure of Example (II-2) using:

10.5 g (26.8 mmol) of tert-butyl N-benzyl-N-methyl-L-isoleucyl-D-hydroxyisovalerate and 250 ml of methylene chloride.

8.5 g (94.5% of theory) of N-benzyl-N-methyl-L-isoleucyl-D-hydroxyisovaleric acid are obtained and can be reacted further without further purification.

EI MS m/z (%): 335 (M$^+$,1); 278 (19); 190 (PhCH$_2$—NMe—CH—CHMeCH$_2$Me,100); 91 (PhCH$_2$,84)

Example (VI-1)

tert-Butyl N-methyl-L-phenylalanyl-D-hydroxyvalerate

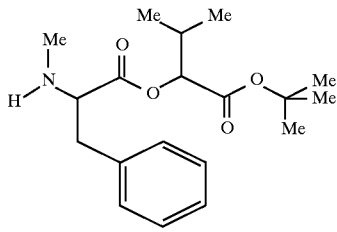

N-terminal deblocking is carried out analogously to the reaction procedure of Example (III-2) using:

10.0 g (23.5 mmol) of tert-butyl N-benzyl-N-methyl-L-phenylalanyl-D-hydroxyisovalerate, 250 ml of ethanol, and 1.0 g of Pd(OH)$_2$/charcoal [Pd content 20%].

7.5 g (95.2% of theory) of tert-butyl N-methyl-L-phenylalanyl-D-hydroxyvalerate are obtained and can be reacted further without further purification.

$^1$H NMR (400 MHz, CDCl$_3$, δ): 0.80, 0.85 (2d, 6H, 2×—CH$_3$; J=6.9 Hz); 1.46 (s, 9H, —C(CH$_3$)$_3$); 2.42 (s, 3H, —N—CH$_3$); 2.94; 2.97 (2d, 2H, —CH$_2$-Phe); 3.55 (m, 1H, —O—CH); 4.58 (d, 1H, —N—CH; J=4.7 Hz); 7.18–7.26 (m, 5H, aromatic —H) ppm EI MS m/z (%): 336 (M$^+$+H,7); 335 (M$^+$,2); 262 (M$^+$–O—CMe$_3$,12); 188 (100); 134 (81)

Compounds of the general formulae (IV), (V) and (VI) which are listed in Tables 4, 5 and 6 below can be analogously in the form of the L-D stereoisomers.

TABLE 4

Examples of compounds of the general formula (IV)

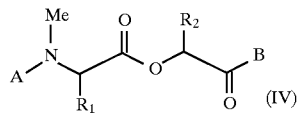

| Ex. No. | A | $R^1$ | $R^2$ | B | Physical Data[a] |
|---|---|---|---|---|---|
| IV-2 | —CO—O—CH$_2$—Ph | —CHMeCH$_2$Me | —CHMe$_2$ | —O—CMe$_3$ | |
| IV-3 | —CO—O—CH$_2$—Ph | —CHMeCH$_2$Me | —CHMe$_2$ | —OH | |
| IV-4 | —CO—O—CH$_2$—Ph | —CHMeCH$_2$Me | —Me | —O—CMe$_3$ | 407 (M$^+$,7) |
| IV-5 | —CO—O—CH$_2$—Ph | —CHMeCH$_2$Me | —Me | —OH | |
| IV-6 | —CH$_2$—Ph | —CH$_2$CHMe$_2$ | —Me | —O—CMe$_3$ | 363 (M$^+$,1) |
| IV-7 | —CH$_2$—Ph | —CH$_2$CHMe$_2$ | —Me | —OH | 307 (M$^+$,7) |
| IV-8 | —CH$_2$—Ph | —CH$_2$—Phe | —Me | —O—CMe$_3$ | 397 (M$^+$,2) |
| IV-9 | —CH$_2$—Ph | —CH$_2$—Phe | —Me | —OH | |
| IV-10 | —CH$_2$—Ph | —CH$_2$CHMe$_2$ | —CHMe$_2$ | —O—CMe$_3$ | 391 (M$^+$,1) |
| IV-11 | —CH$_2$—Ph | —CH$_2$CHMe$_2$ | —(CH$_2$)$_3$—Me | —O—CMe$_3$ | 405 (M$^+$, 5) |

[a] FAB MS or EI-MS m/z (%)

TABLE 5

Examples of compounds of the general formula (V)

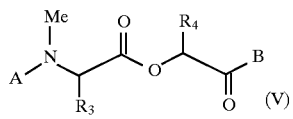

| Ex. No. | A | $R^3$ | $R^4$ | B | Physicla Data[a] |
|---|---|---|---|---|---|
| V-2 | —CH$_2$—Ph | —CH$_2$CHMe$_2$ | —CH$_2$—Ph | —O—CMe$_3$ | 1.44 (—C$\underline{Me}_3$); 2.21 (—N—$\underline{Me}$) |
| V-3 | —CH$_2$—Ph | —CH$_2$CHMe$_2$ | —CH$_2$—Ph | —OH | |
| V-4 | —CH$_2$—Ph | —CHMeCH$_2$Me | —CHMe$_2$ | —O—CMe$_3$ | 1.50 (—C$\underline{Me}_3$); 2.28 (—N—$\underline{Me}$) |
| V-5 | —CH$_2$—Ph | —CHMeCH$_2$Me | —Me | —O—CMe$_3$ | 1.49 (—C$\underline{Me}_3$); 2.26 (—N—$\underline{Me}$) |
| V-6 | —CH$_2$—Ph | —CHMeCH$_2$Me | —Me | | |

[a] $^1$H NMR(400 MHz, CDCl$_3$, δ) in ppm, in each case singlet

TABLE 6

Examples of compounds of the general formula (V)

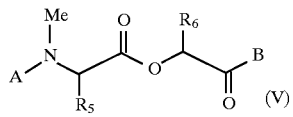

| Ex. No. | A | $R^5$ | $R^6$ | B | Physical Data[a] |
|---|---|---|---|---|---|
| VI-2 | —CH$_2$—Ph | —CH$_2$—Ph | —CHMe$_2$ | —O—Me$_3$ | 1.49 (—CMe$_3$); 2.41 (—N—Me) |
| VI-3 | —H | —CH$_2$—Ph | —Me | —O—CMe$_3$ | 1.48 (—CMe$_3$); 2.42 (—N—Me) |
| VI-4 | —H | —CHMeCH$_2$Me | —Me | —O—CMe$_3$ | |

[a] $^1$H NMR (400 MHz, CDCl$_3$, δ) in ppm; in each case singlet

We claim:

1. A method of combatting endoparasites which occur in humans or in animals which comprises administering to such humans or animals an amount effective therefor of a cyclic depsipeptide having 18 ring atoms of the formula (I)

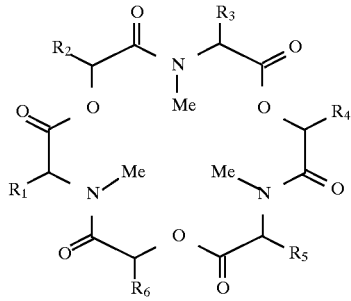

in which

R¹, R², R³, R⁴, R⁵ and R⁶ represent C₁–C₈-alkyl, C₃–C₇-cycloalkyalkyl and phenyl-C₁–C₄-alkyl which phenyl-C₁–C₄-alkyl may be substituted on the phenyl portion by substituents selected from the group consisting of halogen, hydroxyl, C₁–C₄-alkoxy and C₁–C₄-alkyl.

or an optical isomer or racemate thereof.

2. A method of combating endoparasites which occur in human or animal which comprises administering to such humans or animals an amount effective therefor of a cyclic depsipeptide having 18 ring atoms of the formula (I)

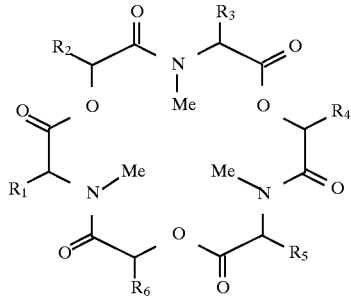

having one of the following combinations of R¹, R², R³, R⁴, R⁵ and R⁶

| R¹ | R² | R³ | R⁴ | R⁵ | R⁶ |
|---|---|---|---|---|---|
| -iBu | -Bn | -iBu | -Bn | -iBu | -Me |
| -nBu | -Me | -sBu | -Me | -sBu | -Me |
| -Me | -Me | -sBu | -Me | -sBu | -Me |
| -nPr | -Me | -sBu | -Me | -sBu | -Me |
| -sBu | -Me | -sBu | -Me | -Bn | -Me |
| -iPr | -Me | -sBu | -Me | -sBu | -Me |
| -nBu | -Me | -nBu | -Me | -nBu | -Me |
| -nPr | -Me | -nPr | -Me | -nPr | -Me |
| -iPr | -Me | -iPr | -Me | -iPr | -Me |
| -sBu | -nBu | -sBu | -Me | -sBu | -Me |
| -sBu | -Bn | -sBu | -Bn | -sBu | -Me |
| -Me | -Me | -iBu | -Me | -iBu | -Me |
| -sBu | -Me | -Me | -Me | -Me | -Me |
| -iBu | -Me | -sBu | -Me | -Me | -Me |
| -Me | -Me | -iPr | -Me | -iPr | -Me |
| -nPr | -Me | -Me | -Me | -sBu | -Me |
| -iPr | -Me | -Me | -Me | -sBu | -Me |
| -iBu | -Me | -Me | -Me | -sBu | -Me |
| -iBu | -Me | -Me | -Me | -Me | -Me |
| -sBu | -Bn | -Me | -Me | -Me | -Me |
| -sBu | -iPr | -Me | -Me | -Me | -Me |
| -sBu | -iPr | -sBu | -Me | -Me | -Me |
| -sBu | -Me | -Chm | -Me | -sBu | -Me |
| -Me | -iPr | -sBu | -iPr | -sBu | -Me |
| -iBu | -Me | -iBu | -Chm | -iBu | -Me |
| -Me | -Me | -sBu | -Me | -Et | -Me |
| -Me | -Me | -sBu | -Chm | -sBu | -Me |
| -Me | -Me | -sBu | -Chm | -Me | -Me |
| -Et | -Me | -sBu | -Me | -sBu | -Me |

Bn: -benzyl; Bu: -butyl; Chm: -cyclohexylmethyl; Et: -ethyl; Me: -methyl; Pr: -propyl i and s: iso and secondary or an optical isomer or racemate thereof.

3. Endoparasiticidal compositions, comprising at least one cyclic depsipeptide having 18 ring atoms of the formula (I)

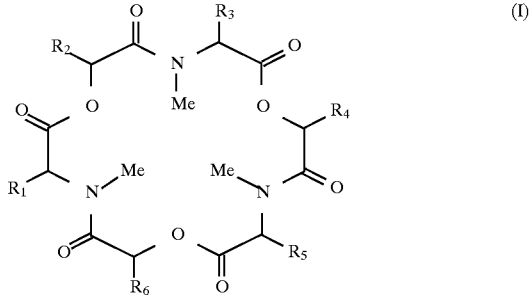

having one of the following combinations of R¹, R², R³, R⁴, R⁵ and R⁶

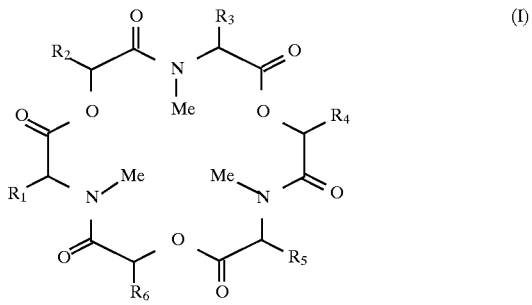

Bn: -benzyl; Bu: -butyl; Chm: -cyclohexylmethyl; Et: -ethyl; Me: -methyl; Pr: -propyl i and s: iso and secondary or an optical isomer or racemate thereof.

* * * * *